United States Patent
Keyes et al.

(10) Patent No.: US 10,444,244 B2
(45) Date of Patent: Oct. 15, 2019

(54) MICROFLUIDIC ARRAY SUPPORTING A LIPID BILAYER ASSEMBLY

(71) Applicant: DUBLIN CITY UNIVERSITY, Dublin (IE)

(72) Inventors: Tia Keyes, Dublin (IE); Robert Forster, Dublin (IE); Hajra Basit, Dublin (IE); Sean Maher, Dublin (IE); Vincent Gaul, Dublin (IE)

(73) Assignee: DUBLIN CITY UNIVERSITY, Dublin (IE)

( * ) Notice: Subject to any disclaimer, the term of this patent is extended or adjusted under 35 U.S.C. 154(b) by 109 days.

(21) Appl. No.: 15/321,598

(22) PCT Filed: Jul. 2, 2015

(86) PCT No.: PCT/EP2015/065163
§ 371 (c)(1),
(2) Date: Dec. 22, 2016

(87) PCT Pub. No.: WO2016/001391
PCT Pub. Date: Jan. 7, 2016

(65) Prior Publication Data
US 2017/0176449 A1 Jun. 22, 2017

(30) Foreign Application Priority Data

Jul. 3, 2014 (GB) .................................... 1411915

(51) Int. Cl.
*G01N 33/48* (2006.01)
*B01L 3/00* (2006.01)
*G01N 33/68* (2006.01)
*G01N 33/543* (2006.01)
*G01N 33/554* (2006.01)
*G01N 33/487* (2006.01)
*B01L 9/00* (2006.01)
*G01N 27/02* (2006.01)

(52) U.S. Cl.
CPC .... *G01N 33/6842* (2013.01); *B01L 3/502707* (2013.01); *B01L 3/502715* (2013.01); *B01L 9/527* (2013.01); *G01N 27/026* (2013.01); *G01N 33/48721* (2013.01); *G01N 33/5432* (2013.01); *G01N 33/54366* (2013.01); *G01N 33/554* (2013.01); *B01L 2200/12* (2013.01); *B01L 2300/0848* (2013.01); *B01L 2300/0858* (2013.01); *B01L 2300/12* (2013.01); *B01L 2300/165* (2013.01)

(58) Field of Classification Search
CPC .. G01N 3/6842; G01N 33/6803; G01N 33/68; G01N 33/50; G01N 33/48; G01N 33/6842; B01L 3/5027; B01L 3/5027; B01L 3/502; B01L 3/50
USPC .......................................... 422/502, 500, 50
See application file for complete search history.

(56) References Cited

U.S. PATENT DOCUMENTS

2006/0147993 A1   7/2006   Carre et al.

FOREIGN PATENT DOCUMENTS

CN   103289119 A   9/2013
WO   2006/104639 A2   10/2006

OTHER PUBLICATIONS

Mallon et al, Fabrication of gold sphere to cuboid nanoarrays using PDMS templates, Chem. Commun., 2011, 47, 7605-7607. (Year: 2011).*
Basit, H. et al, Aqueous—filled polymer microcavity arrays: versatile & stable lipid bilayer platforms offering high lateral mobility to incorporate membrane proteins, The Royal Society of Chemistry, 2012, 1-6. (Year: 2012).*
Jose et al, Supplemental Materials: Lipid bilayer assembly at a gold nanocavity array, Chem. Commun., 2011, 47, 12530-12532. (Year: 2011).*
Pernites et al, ColloidallyTemplated Two-Dimensional Conducting Polymer Arrays and SAMs: Binary Composition Patterning and Chemistry, ACS Applied Materials & Interfaces, Feb. 2011, 3, p. 817-827. (Year: 2011).*
Jose et al, Lipid bilayer assembly at a gold nanocavity array, Chem. Commun., 2011, 47, 12530-12532. (Year: 2011).*
Abdelsalam et al., "Preparation of Arrays of Isolated Spherical Cavities by Self-Assembly of Polystyrene Spheres on Self-Assembled Pre-patterned Macroporous Films," *Adv. Mater.* 16(1):90-93, Jan. 5, 2004.
Basit et al., "Aqueous-filled Polymer Microcavity Arrays: Versatile & Stable Lipid Bilayer Platforms Offering High Lateral Mobility to Incorporated Membrane Proteins," *Analyst* 140:3012-3018, 2015.
Forster et al., "Detecting Disease Biomarkers Using Nanocavities and Nanoparticle Composites," *Sensors & Their Applications XVI, Journal of Physics: Conference Series* 307, 2011, 6 pages.
Galeotti et al., "Precise Surface Patterning of Silk Fibroin Films by Breath Figures," *Soft Matter* 8:4815-4821, 2012.
Jose et al., "Lipid Bilayer Assembly at a Gold Nanocavity Array," *Chem. Commun.* 47:12530-12532, 2011.
Moreno et al., "The Membrane-Activity of Ibuprofen, Diclofenac, and Naproxen: a Physico-Chemical Study with Lecithin Phospholipids," *Biochimica et Biophysica Acta* 1788:1296-1303, 2009.
Widawski et al., "Self-Organized Honeycomb Morphology of Star-Polymer Polystyrene Films," *Nature* 369:387-389, Jun. 2, 1994.

(Continued)

*Primary Examiner* — Christine T Mui
(74) *Attorney, Agent, or Firm* — Cozen O'Connor

(57) ABSTRACT

A microfluidic array supporting a lipid bilayer assembly on which membrane proteins can be assembled is described. The array is formed from a hydrophilic polymeric substrate or metal substrate comprising a planar surface with a plurality of individual spherical depressions formed therein. Each of the depressions are configured to have a diameter greater than 1 µm and containing an aqueous solution. Across each of the depressions is provided a lipid layer. Each of the plurality of individual depressions comprise arcuate side walls extending downwardly into the substrate from the planar surface.

10 Claims, 17 Drawing Sheets

(56) References Cited

OTHER PUBLICATIONS

International Search Report, dated Oct. 9, 2015, for PCT/EP2015/065163, 5 pages.
Written Opinion, dated Oct. 9, 2015, for PCT/EP2015/065163, 6 pages.
Combined Search and Examination Report under Sections 17 and 18(3), dated Mar. 25, 2015, for corresponding GB Application No. GB1411915.0, 7 pages.
Lazzara et al., "Separating Attoliter-Sized Compartments Using Fluid Pore-Spanning Lipid Bilayers," *ACS Nano* 5(9):6935-6944, 2011.
Torres et al., "Functional single-cell analysis of T-cell activation by supported lipid bilayer-tethered ligands on arrays of nanowells," *Lab Chip* 13:90-99, 2013.

\* cited by examiner

MICROFLUIDIC ARRAY SUPPORTING A LIPID BILAYER ASSEMBLY

FIELD

The present application relates to structures which can be used as reliable and reproducible models of cell membranes into which membrane proteins can be assembled. The application particularly relates to a microfluidic array supporting a lipid bilayer assembly on which membrane proteins can be assembled. The present teaching may also find application within the context of mimicking membranes of organelles.

BACKGROUND

Membrane proteins (MPs) constitute nearly one third of all human proteins and are known to orchestrate key cellular functions ranging from ion transport, cell-cell attachment, to signaling. Consequently, such proteins are important targets in pharmaceutical drug discovery. However, despite their importance, the direct in vitro study of membrane proteins lacks suitable high throughput screening models, which can be reproducibly fabricated, with controlled lipid composition and where the structural integrity of the protein is preserved upon reconstitution. Bio-appropriate model environments that are simple to construct and are suitable for chip-based applications still remain an important challenge. A key feature of the cell membrane, which is important in membrane protein function is its inherent 2-D fluidity. Lateral diffusion of lipids and membrane proteins within the membrane regulate the distribution of membrane components and affects many processes, such as formation of protein complexes and the dynamic assembly/disassembly lipid disordered and ordered microdomains. Thus, for any artificial bilayer model to be credible, it must exhibit the property of high lateral mobility of lipid and protein constituents.

To this end, while Supported Lipid Bilayers (SLBs) are valuable artificial bilayer models, an inherent major drawback is the interaction of the bilayer with the solid substrate, which dramatically lowers the mobility of the lipids and the incorporated membrane proteins compared with native cell membranes or free liposomes. A number of approaches have been taken to address this issue including, Tethered Bilayer Lipid Membranes (t-BLMs) in order to minimize these interactions by the inclusion of a spacer between the bilayer and the surface. Although t-BLMs were shown to provide better stability to the lipid bilayers, diffusion coefficients of the lipids measured were not significantly improved compared to those measured for SLBs on planar substrates and the same is true for cushioned SLBs. In order to obtain lipid bilayers that are sufficiently separated from the underlying substrates, another approach is to span lipid bilayers across nano- and micro-sized apertures, forming the so-called Black Lipid Membranes (BLM). BLMs however, suffer poor stability due to the retention of organic solvents that are commonly used in their preparation. Moreover, the incorporation and stability of membrane proteins is severely limited owing to their unfavorable mode of preparation and the remnant solvents within the bilayer.

The design of solvent free methods for pore-spanning lipid bilayers is also known in the art. However, most such techniques function in restricted conditions such as the use of certain size of the pores and the vesicles, application of sheer flow and pH, the use of Giant Unilamellar Vesicles (GUVs) or spanning over dry substrates. While each of these methods has shed light on the mechanisms of a variety of pore-spanning lipid membranes, the incorporation and manipulation of membrane proteins within these systems still remains a daunting task.

Typically the best alternatives used are live cell assays. However, these are expensive to implement because of costs associated with cell culture. So an intervening step where the membrane interactions, protein interactions in a biomimetic environment and/or transmembrane transport can be assessed in advance of more complex pre-clinical assessment could offer significant savings.

Porous array structures have been described, e.g. WO2006/104639 describes a porous array where the pores are all sub-micron in dimension. Chemical Communications vol. 47, 2011, 'Lipid bilayer assembly at a gold nanocavity array' pp. 12530-12532 Jose et al demonstrates the use of nano-dimensioned pores on arrays with diameters <800 nm. However the limitation of all these structures is that they are sub-micron and to date there have been significant challenges to obtain a bilayer which spans apertures greater than 1 micron.

SUMMARY

Accordingly, a chamber and method as defined in the claims is provided.

BRIEF DESCRIPTION OF THE DRAWINGS

The present application will now be described with reference to the accompanying drawings in which:

FIG. 12 (B) a comparison of the autocorrelation curves for lipid diffusion of a bilayer of DOPC (1% mol/mol labelled DOPE-BODIPY) supported on 2.8 micron PDMS cavities in the presence and absence of 4 mMol ibuprofen.

DETAILED DESCRIPTION OF THE DRAWINGS

In accordance with the present teaching, a microfluidic nanopore array having dimensions ranging from the sub to micron level and supporting a spanning lipid layer (or bilayer) and reconstituted membrane proteins enclosed therein is provided. Such an array could be provided with nano or micropores. The array comprises a lipid layer or bilayer spanned over micrometer or nanopore sized buffer-filled hemispherical cavities formed in this exemplary arrangement on hydrophilic polydimethylsiloxane (PDMS). A bilayer prepared using Langmuir Blodgett or Langmuir Blodgett Schaeffer technique or (particularly in the case of protein containing bilayers) a combination of Langmuir-Blodgett and vesicle fusion techniques is used to obtain a defect-free layer (or bilayer) that spans the cavities. A range of cavity sizes from 620 nm to 5 micrometers can be reliably spanned using this technique and the spanned bilayers remain intact and stable for several days.

An array per the present teaching can be used to assemble a spanning lipid layer or bilayer into a flow cell that is directly mounted onto a microscope. While the present teaching can be used at a sub-micron level, for example in the range of 620 nm to 1 micron, it will be appreciated that it has significant application in the provision of lipid bilayers that span pores greater than 1 micron. As will be evident from the following discussion, such arrangements require a micropore which have a pore height to aperture diameter ratio greater than one, i.e the shape of the micropore is at least a little over a hemisphere. For example a 3 micron cavity if it is formed with a pore opening above the equator of the sphere might have an opening of say 2 micron, so the height to aperture ratio is 3/2. The present inventors have realized that if the pore has dimensions greater than 1 micron that the pore must be a truncated sphere so as to support the lipid bilayer in a stable form for periods of days.

Figure 1A:
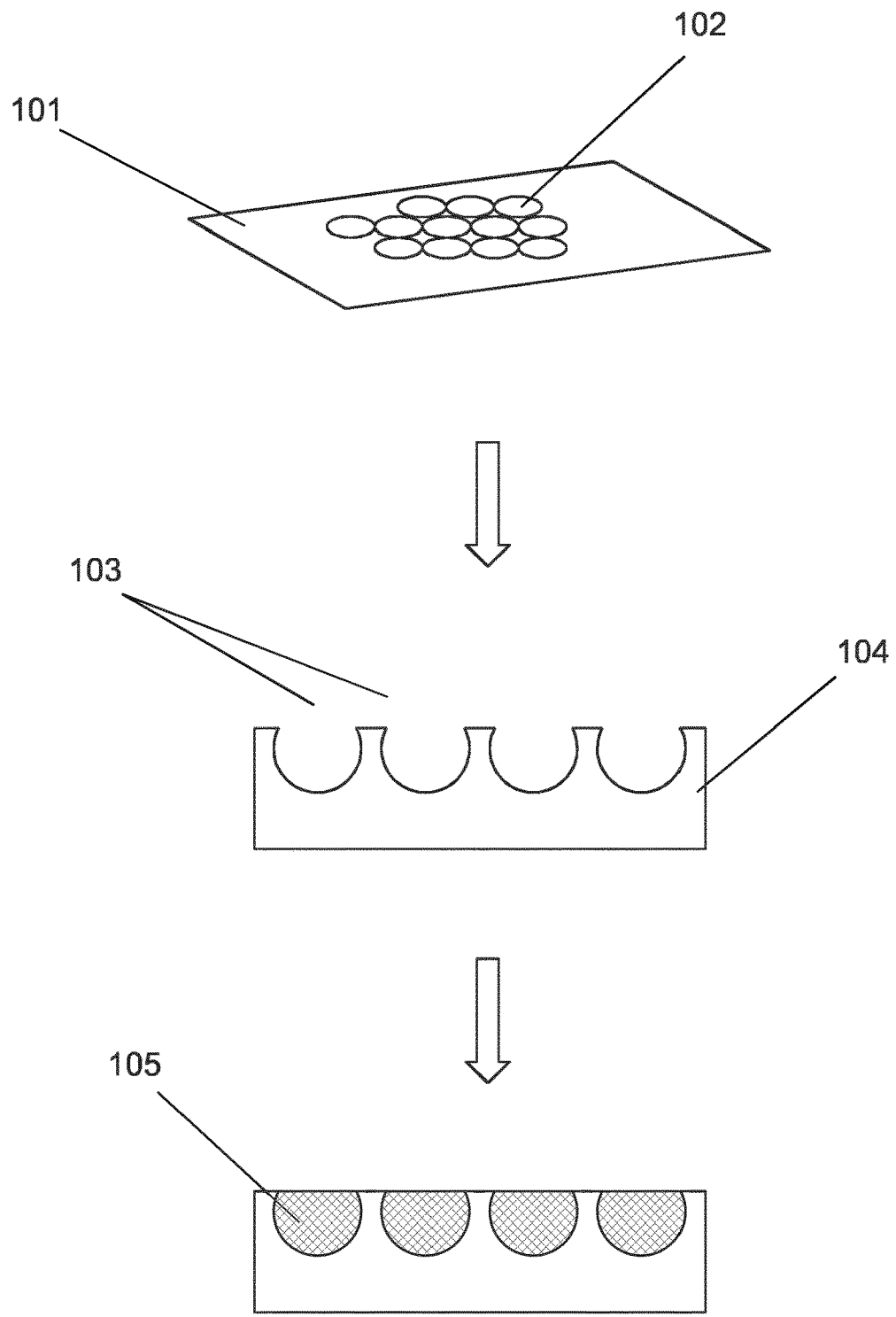
FIGS. 1A and 1B provide a schematic illustration of the steps involved in the formation of an array having free-spanning lipid layers over buffer-filled microcavities.
Figure 1B:
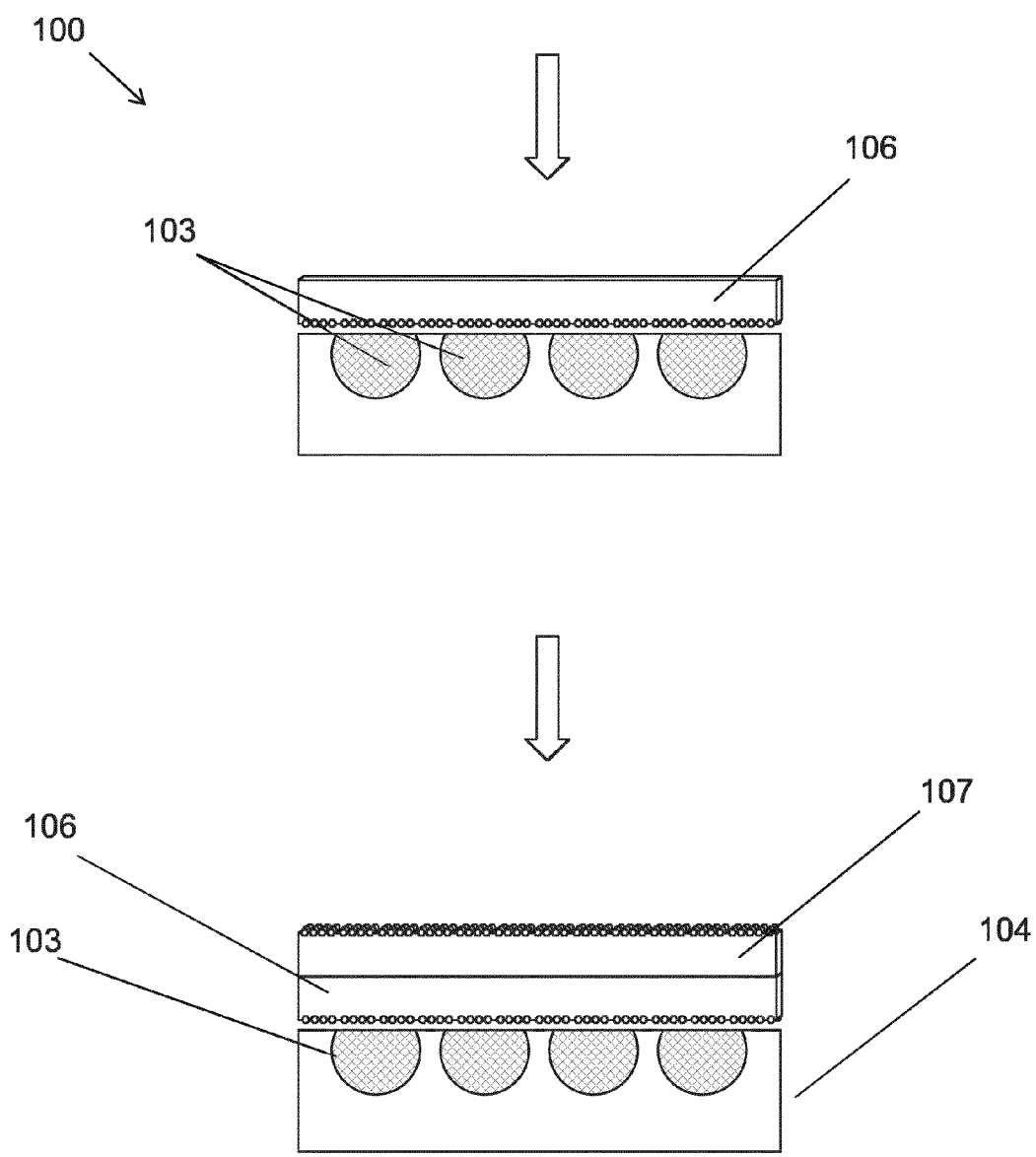

The present teaching will now be described with reference to an exemplary route to preparation of the array 100 as shown in FIGS. 1A and 1B.

As shown in FIG. 1A, a polymer (e.g. PDMS) substrate is prepared by spherical particle deposition of spheres 102 onto a slide 101 of glass, mica, quartz, metal coated substrate or silicon wafer. Specifically, an ordered array of colloidal polystyrene spheres 102 is allowed to self-assemble into a close packed array on the slide 101. This array of spheres 102 is then coated with PDMS (polydimethylsiloxane). After curing, the PDMS is peeled off or removed from the slide 101. The PDMS is inverted to reveal a close packed array of imprinted cavities 103 in the PDMS substrate 104. Effectively the close packed array on the slide forms a template for the ultimate patterning of the PDMS substrate. The dimensions of the spheres 102 used in the templating process determines the ultimate size of the nanopores that are formed in the surface of the PDMS substrate.

A diameter of 600 nm has been found suitable for the spheres 102 but any diameter in accordance with the size of the cavity desired may be chosen as appropriate by the skilled person. The slide 101 and array of spheres 102 may reused for manufacture of more PDMS substrates 104 having cavities 103 therein.

After separation of the PDMS substrate 104 and the slide 101, the substrate 104 is rendered hydrophilic by plasma treatment at controlled air pressure for 5 minutes. Of course, the skilled person can choose the duration of the treatment as appropriate and the subject teaching should not be considered limited to 5 minutes.

The cavities 103 in the substrate 104 are then filled by sonication with a solution 105, e.g. buffered for 30-45 minutes. As will be explained in more detail below, in order for optimal lipid layer/bilayer assembly, the pores should be filled with the aforementioned solution 105. This solution 105 is typically aqueous for example water alone or aqueous solution containing salt and or sugar and/or buffer, e.g. ionic strength or pH buffer.

With reference to FIG. 1B, assembly of a lipid layer 106 over the array 100 of cavities 103 is then carried out. This may be achieved by assembling the lipid layer 106 by the known Langmuir-Blodgett (LB) or LB Schaefer (LBS) method to form the lipid layer 106. It will be appreciated that a Langmuir-Blodgett method contains the deposition of one or more monolayers of an organic material from the surface of a liquid onto a solid by immersing (or emersing) the solid substrate into (or from) the liquid. A monolayer is adsorbed homogeneously with each immersion or emersion step, thus films with very accurate thickness can be formed. This thickness is accurate because the thickness of each monolayer is known and can therefore be added to find the total thickness of a Langmuir-Blodgett film.

The formed lipid layer 106 is of a selected composition which may be a single lipid or complex mixture of lipids. For optical studies, e.g. FLCS or FCS, the lipid may be labelled. For example 1% mol/mol of the appropriate dye labelled DOPE is spread in the lipid layer 106. It will be appreciated that labelling the lipid is done if one wants to study the dynamics of the lipid. However, as will be explained in more detail below, when protein study is required, proteins can be labelled or both proteins and lipids can be labelled. The labelled lipid does not have to labelled during the LB deposition it, can be introduced with a liposome fusion step if this takes place. The labelled lipid can also be introduced by self-assembly into the layer after bilayer assembly-particularly useful if one wants asymmetric labelling. As will be explained in more detail, a liposome fusion step is typically done if introducing a protein to the array.

Optionally, the formation of the first lipid layer 106 may be followed by deposition of a second lipid layer 107 on top of the first layer 106 to form a lipid bilayer 106, 107. The formation of the second lipid layer 107 may be achieved either by a second LB or LBS step or by fusion of liposomes over the first layer 106. Fusion is where a liposome (aka vesicle) is disrupted on top of the first lipid layer 106 (or bilayer 106,107) formed by LB. As mentioned above when a protein is introduced to the array, a liposome fusion step is typically used. If there is a desire to provide asymmetric layers, the LB assembly can provide a different lipid composition to the array for the first 106 and second 107 layers. For example, the liposome composition of the second layer 107 can vary from that of the first LB deposited layer 106.

The cavities may be considered depressions in the planar surface of the substrate 104. It should also be noted that the shape of the cavities is important in that each of individual cavities comprises arcuate side walls extending downwardly into the substrate from the planar surface. In this way the depressions define a truncated sphere, sometimes referred to as a spherical dome or spherical cap. Such structures are defined by a portion of a sphere that is cut off by a plane. In the context of the present teaching, desirably these depressions have a geometry whose pore height to aperture diameter is greater than one, i.e. the well defined by the depression is deeper than its opening at the top. In particular, at the top or opening of the cavities where an aperture providing access to the depression is defined, the walls are approaching each other i.e., the diameter of the opening or aperture is smaller than the diameter of the cavity defined by the pore. It has been found that this shape is most suitable for assembly of a lipid layer 106 over the array 100 of cavities 103 as it provides more support to the lipid layer than straight wall cavities. Furthermore, it has been found that if the edges of the cavities 103 are curved rather than sharp, this ensures that the lipid layer is not perforated by the sharp edges. Use of such arrangements having a diameter of greater than 1 micron have been found by the present inventors as being capable of supporting lipid bilayers in a stable form for periods of time of more than a few hours, indeed stability of the order of days has been found.

One of the advantages of the cavities 103 in accordance with the present teachings, is that concentration gradients can be created, e.g. osmotic or ionic across the bilayer by filling the cavities 103 with a different solution (e.g. salt, pH or sugar) concentration to an external contacting solution.

The above outlined method for construction of the array has been performed by the inventors of the subject application for lipid layer and bilayer assembly across a broad range of lipid compositions, including simple dioleylphosphatidylcholine (DOPC) layers to complex ternary assemblies containing PS, DOPC DOPS, cholesterol and Sphingomyelins, through LB assembly followed by vesicle disruption (liposome fusion). Vehicle disruption introduces a liposome or proteoliposome to the lipid layer 106 which disrupts on contact with the layer to form the second layer (or leaflet) 107 of the lipid bilayer 106, 107 at the surface.

Having formed a lipid layer/bilayer on the substrate, the resultant structure shares many features with a cell membrane and may be considered an artificial cell membrane.

Having fabricated this artificial cell membrane, it is possible to introduce proteins into the lipid layers/bilayers. As a result these artificial cell membranes provide powerful new models to study the behaviour of such proteins in highly bio-relevant environments. Where described with reference to liposomes it will be appreciated that arrays per the present teaching may be extended to accommodate other forms of membrane mimics such as nanodiscs which are disc-shaped, nanoscale, phospholipid bilayers surrounded by two molecules of an amphipathic alpha-helical protein that surround the bilayer disc like a belt and limit its size It will be appreciated and understood that the general term membrane proteins includes transmembrane and peripheral proteins which are all membrane associated. Where the following description makes reference to transmembrane proteins it will be appreciated that this is to provide detail of an exemplary implementation of the present teaching and is not intended to limit application to only transmembrane proteins.

In this context, FIGS. 1A and 1B describe a sequence of steps where a transmembrane protein assembly is provided by filling cavities 103 with proteoliposomes prior to forming the lipid layer/bilayer over the cavity. Proteoliposomes are prepared by reconstitution of a membrane protein into a liposome using detergent followed by removal of the detergent using biobeads.

An example of a protocol for integrin achieving this is now described: Lipid in chloroform of the desired composition is dried under a steady stream of nitrogen in a glass vial before being placed under vacuum for 2 hours to ensure solvent evaporation. For lipid diffusion studies DOPE-atto655 is also included at 1% mol/mol to lipid. The lipid is then solubilised at 1 mM in a reconstitution buffer (10 mM HEPES, 150 mM NaCl, 1 mM $CaCl_2$, 0.1% Triton X-100, pH 7.4). Labelled integrin (protein) is then added to the vial before the solution is shaken at room temperature for 30 minutes to fully ensure that all lipid has been solubilised and that the solution is homogenous. The solution is then incubated at 37° C. for 1 hour 30 minutes. The detergent is removed by the addition of 100 mg of biobeads per ml of solution for 3 hours 30 minutes in a slowly shaken vial. The biobeads are then removed and replaced by a fresh batch of 100 mg biobeads per ml of solution for 30 minutes (slowly shaken). Once complete, biobeads are removed and the reconstituted proteo-liposomes are stored at 4° C. until use.

Alternatively proteins may be introduced subsequent to formation for example by using the known method of detergent treatment of a pre-formed layer 106 (or bilayer 106,107) with the target protein.

For peripheral proteins, proteins which spontaneously assemble into the layer 106 or bilayer 107 or glycolipids, simple flow through of the protein/glycolipid across the array 100 and incubation is carried out. It will be appreciated that the protein association may demand presence of specific lipids in the presenting layer (e.g. DOPS in the case of prothrombin) and also may demand the presence of calcium ions in the contacting medium, e.g. annexin.

As will be explained in more detail below, using FLCS, a fluorescently labeled protein or lipid can be reliably located by scanning through the Z axis and identifying the position of maximum intensity.

An array formed with reference to FIGS. 1A and 1B can also be used as part of a microfluidic platform. For example, the array 100 can be assembled into a flow through device which permits retention of water over the surface of the substrate 104 and permits introduction of reagents to the lipid layer 106 (or bilayer 106, 107), which can be allowed to sit for a residence period in contact with the lipid bilayer before wash through of materials.

Figure 2A:
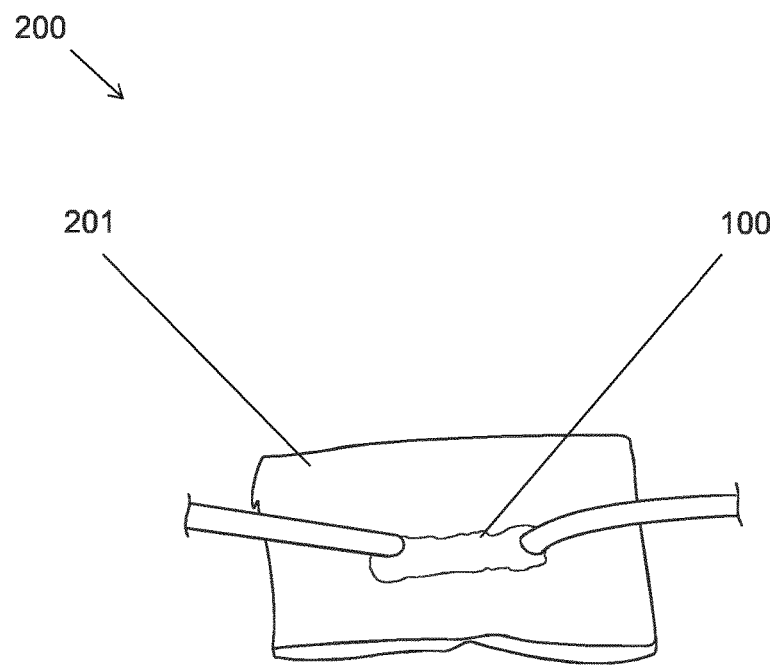
FIG. 2A provides an illustration of a microfluidic platform using the array of FIG. 1.

An example of such a microfluidic platform 200 is illustrated in FIG. 2A and is constructed by initially templating an array 100, per the teaching of FIGS. 1A and 1B. An inlet and outlet hole (not explicitly shown) to allow for the liquid flow may be fabricated built into the PDMS substrate 100 via moulding during formation of the porous array 100. The inlet and outlet may be formed by hole punching the PDMS substrate. The modified, with respect to that shown in FIG. 1, PDMS substrate is then bonded to a solid support 201, typically a microscope cover slip. This then completes the fabrication of the platform. Lipid vesicles containing a dye (for optical experiments) with or without protein are then introduced using the inlet over the formed cavities. It will be appreciated by those skilled in the art that a drug, lectin or ligand can also be introduced to the bilayer or proteobilayer via the microfluidic inlet.

The outlet is required as the solution flowing over the lipid bilayer will overfill the small sample volume. Using the outlet, it is also possible to compare the concentration of a given species introduced over the bilayer (e.g. a drug) in the introduced volume to what comes out of the outlet, as a measure of binding of the species to the bilayer. It will be appreciated that, for example using HPLC, the concentration of material e.g. drug introduced to the bilayer, e.g. after a given residence time, compared with the concentration that is washed through may be determined. Such analysis allows determination of the concentration retained or partitioned into the bilayer.

The DOPC vesicles containing the dye with or without reconstituted protein were then injected into the microfluidic chamber to obtain the free-spanning lipid bilayers.

The influence of external agents, e.g. drugs, buffer, ions other proteins etc. can be examined by flowing these reagents across the lipid bilayer interface using the microfluidic platform 200.

Figure 2B:
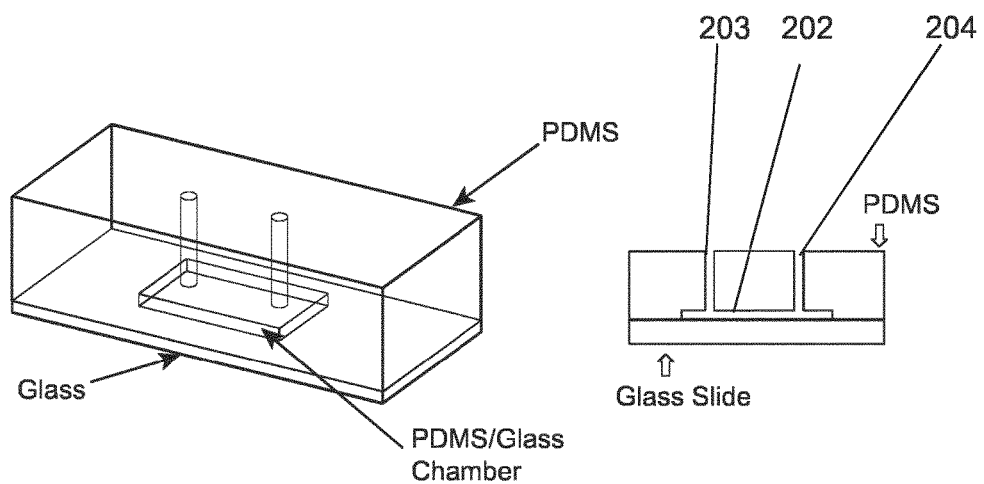
FIG. 2B shows another example of a platform provided in accordance with the present teaching.

FIG. 2B shows a variant to the arrangement illustrated with reference to FIG. 2A. In this configuration a well 202 is moulded into the front face of the PDMS. By providing the well 202, it is possible to provide a fluid channel connected with the inlet 203 and outlet 204 and permits a flow of materials, e.g. drugs/proteins/lectins over the surface of the lipid bilayer of the array 100. Although not visible in FIG. 2B, an array (such as the array 100 of FIG. 1) is built within the channel formed by the well 202.

It will be appreciated that the reference to PDMS in the schematic is exemplary of the type of substrate material that could be used and it is not intended to limit the present teaching to PDMS as other materials such as PMMA could be used for the body of the array. In another configuration PDMS or gold could be used at the array surface. In use, a microscope objective would be presented to and lie at the glass slide interface. Furthermore, the inlet 203 may act as an outlet and the outlet 204 may act as an inlet. It will be appreciated by those skilled in the art that any configuration that allows introduced fluid to make contact with the array, specifically the lipid bilayer, in the well 202 is sufficient.

The presence of a lipid layer 106 (or bilayer 106, 107) spanning the pre-filled cavities 103 can be confirmed by confocal microscopy using a fluorophore. Cavities 103 made from polystyrene spheres with different diameters can be assessed for lipid spanning after pre-filling the cavities with a buffer (e.g., aqueous solution 105) and forming of the layer 106 (or bilayer 106, 107) as described above.

Figure 3:
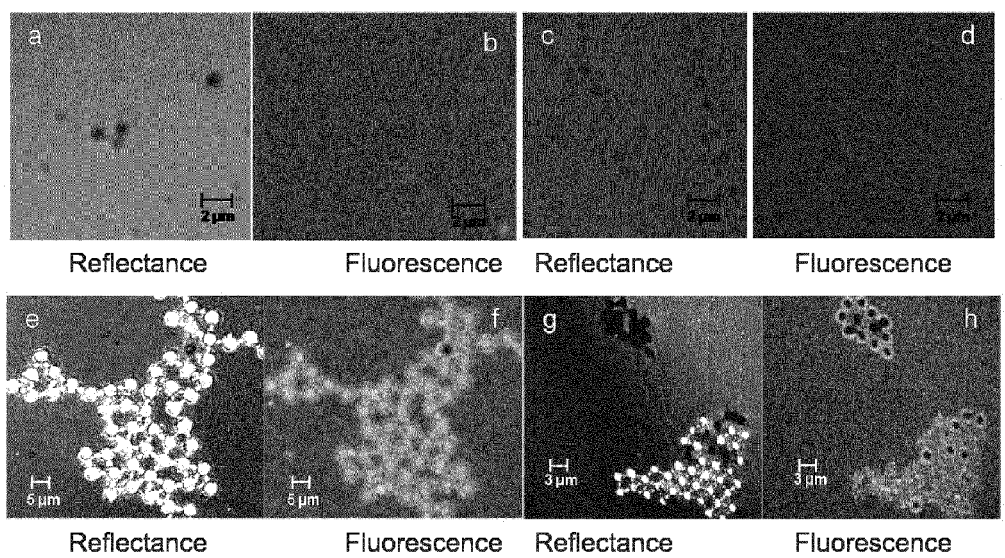
FIG. 3 shows confocal imaging of a fluorescently doped bilayer formed over cavities of different sizes.

FIG. 3 presents confocal images of a fluorescently doped DOPC bilayer 106, 107 spread over filled cavities 103. Cavities 103 of sizes 620 nm (images a & b), 1 μm (images c & d), 3 μm (e & f) and 5 μm (g & h) are used. Bilayers 106, 107 contained 1 mol % DOPE-Carboxyfluorescein as the fluorophore. The excitation wavelength was 488 nm. The fluorescence images (b, d, f and h) were collected using a 505 nm long pass filter, above 505 nm and reflectance images (a, c, e and g) were collected using a 420 nm long pass below 505 nm. Both fluorescence and reflectance images were collected simultaneously using two different channels.

An advantage that can be exploited, because of the spherical nature of the pore array in assessing fluid filling of the arrays 100, is the refractive index difference between PDMS (n≈1.45) and the buffer (n≈1.33). This causes the incident laser light to scatter at the positions of the filled cavities and has the effect of making the filled cavities 103 look significantly brighter than the unfilled ones or the planar PDMS. This is shown in reflection images for the cavity arrays shown in FIG. 3 (a, c, e and g).

It is evident from the images of FIG. 3 that not all the cavities 103 were filled with buffer on sonication. However, the lipid bilayer 106, 107 was observed to span unfilled cavities 103 in the substrate 104 where the cavity diameter was less than 1 μm. This is confirmed from the homogenous fluorescence obtained in fluorescence images b and d respectively, where the reflectance image demonstrates that a number of the cavities 103 are unfilled. In contrast, for the larger cavities i.e. those made from 3 μm and 5 μm spheres (images f and h respectively of FIG. 3), the bilayer 106, 107 was observed to exclusively span the buffer filled cavities 103. When cavities 103 of these dimensions were not pre-filled with a buffer (e.g., aqueous solution 105) the lipid was observed to coat the interior surface of the cavity 103. This result highlights the importance of the presentation of an aqueous interface e.g., aqueous solution 105, across the cavities having aperture diameters exceeding approximately 1 μm.

It will be apparent from inspection of FIG. 3 that the hydrophilic interface (provided by the use of solution 105 in the cavities 103), across which the Langmuir-Blodgett monolayer assembles, is required for formation of a spanning bilayer 106, 107 on the larger diameter cavities 103. Moreover, the Langmuir-Blodgett technique is capable of forming homogenous monolayers over small defects (e.g., smaller diameter cavities 103), whereas for the larger diameter unfilled cavities the LB film formed would be discontinuous and the injected vesicles instead form a bilayer in the interior walls of the cavity 103.

In order to assess the stability of the resulting spanning layers, confocal fluorescence imaging and FCS was performed on the supported bilayers 106, 107 over all cavity 103 sizes over a period of multiple days. The resultant images showed that the lipid bilayers 106, 107 formed over filled cavities 103 using the LB/vesicle fusion method were stable for a period of between 4-5 days and that lipid diffusion coefficient remained stable during this period. This extended stability, which is usually an issue with Black Lipid Membranes or on pores which are not fluid filled or those which are greater than 1 micron in diameter with other shapes, is observed to be alleviated in the present system attributed to the presence of the aqueous reservoir offered by the filled cavities 103 and also to the specific speherical cap shape of these wells.

Examples are now given of the application of the array 100 of the present teachings in study of (i) the fluidity of the spanning lipid bilayers and (ii) reconstituting membrane proteins into the cavity spanning lipid bilayers.

(i) Fluidity of Cavity Supported Lipid Bilayers.

Lateral diffusion co-efficients of a DOPC bilayer at the arrays 100 was studied to establish the fluidity of a spanning lipid bilayer 106, 107. Although the following example is described with reference to bilayers 106, 107, a single lipid layer e.g., layer 106 may also be used.

The diffusion coefficient of lipids assembled over the cavities 103 and at planar regions on the PDMS substrate 104 were compared. To this end, Fluorescence Lifetime Correlation Spectroscopy (FLCS) and/or fluorescence correlation spectroscopy (FCS) was employed to study bilayers spread in a similar manner as described with reference to FIG. 3, with the exception that for FLCS, the bilayers were tagged with a DOPE-Atto-655 dye at a concentration of 1 nM, which is approximately equivalent to a ratio of 1:100,000 dye:lipid. The lower dye concentration is required for FLCS experiments. To accurately locate the bilayer 106, 107 and the cavity 103 spanning bilayers 106, 107 in the FLCS experiment both reflectance and fluorescence lifetime (FLIM) images were recorded.

Figure 4:
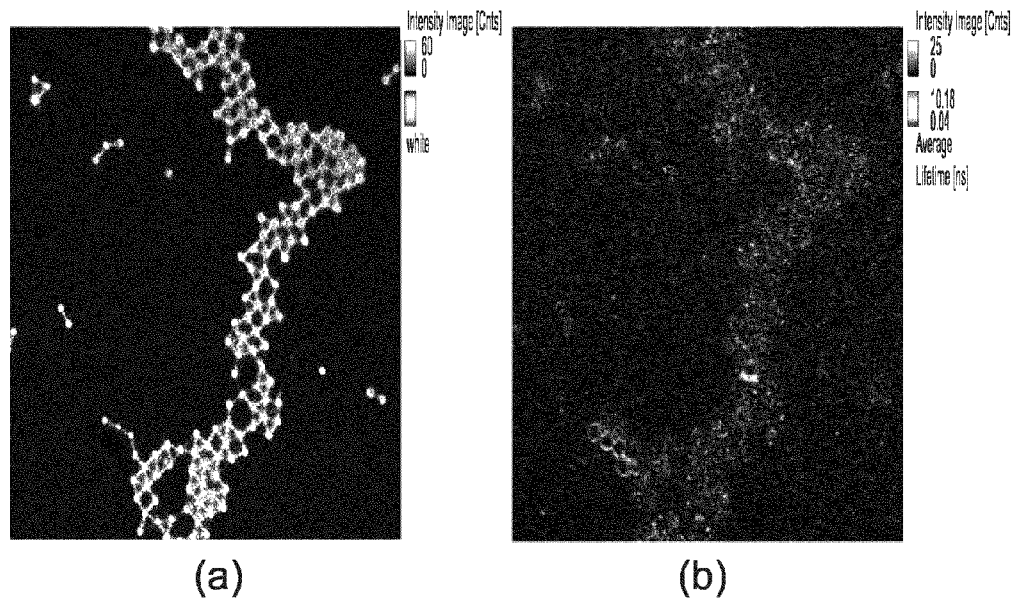
FIG. 4 shows FLIM images (a) reflectance and (b) fluorescence obtained for lipid spanning cavities with a diameter of 3 µm.

FIG. 4 shows FLIM images (a) reflectance and (b) fluorescence obtained for lipid spanning cavities made using 3 μm spheres. The fluorophore used is the aforementioned ATTO 655-DOPE at 1 nM concentration and the image size is 80×80 μm.

Figure 5:
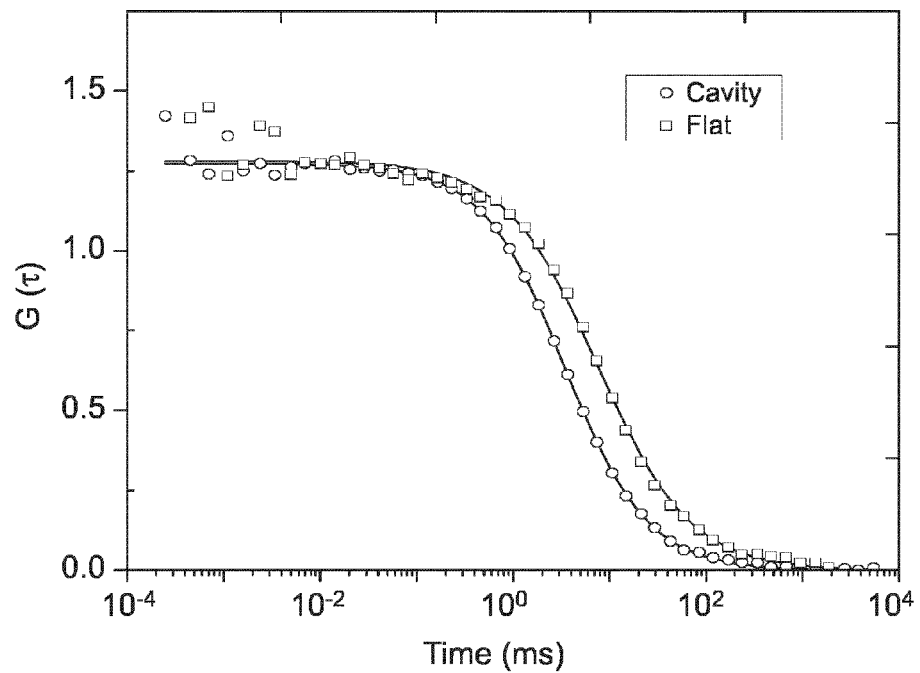
FIG. 5 shows normalized autocorrelation curves measured above a 3 µm cavity, and on the flat regions of the supported bilayer.

As can be seen from images (a) and (b) of FIG. 4, the reflectance images were effective guides to locating filled-cavity spanning bilayers over 3 μm cavities. FLCS measurements were recorded over cavities as well as flat PDMS surfaces to obtain the autocorrelation functions for each surface. These curves are shown in FIG. 5 as will be described in more detail below. The autocorrelation curves obtained were fit to the 2-dimensional model described in equation 1 to obtain the lateral diffusion co-efficient of the lipids in the bilayer.

$$G(\tau) = \frac{1}{N}\left[1 + \left(\frac{\tau}{\tau_i}\right)^{\alpha}\right]^{-1} \quad (1)$$

where, $G(\tau)$ is the autocorrelation function, N is the average number of fluorescent molecules present in the confocal volume, $\tau_i$ is the characteristic residence time, and $\alpha$ is the anomalous parameter which reflects the extent of deviation of diffusion from normal or Brownian motion where $\alpha=1$, i is the index of the components. The lateral diffusion coefficient, $D_L$, can be obtained as $D_L=\omega^2/4\tau_i$. In this equation, $\omega$ is the radius of the laser beam used. To determine $\omega$ for each excitation, a reference solution of free dye was used for which the diffusion coefficient is known. For excitation at 640 nm, the reference dye was Atto-655 in water at 25° C. and its diffusion coefficient is 426 pmt s$^{-1}$.

FIG. 5 shows the normalized autocorrelation curves measured above a 3 μm spanning cavity (solid circular symbols), and on the flat regions of the supported bilayer (rectangular symbols). These are calculated from measurements acquired with 640 nm Laser. The fluorophore observed here is the ATTO 655-DOPE at 1 nM concentrations. The solid lines passing over the points represent the fits using equation (1).

From FLCS, the diffusion co-efficient obtained for the lipid bilayer supported over the planar region of the hydrophilic PDMS was found to be 4.1±0.6 μm$^2$/s with an value approximately equal to 1 i.e. =0.997±0.002. The lipid diffusion coefficient over flat regions of the PDMS was found to be self-consistent across multiple sites across multiple samples of different cavity sizes. The value reflects the high hydrophilicity of the plasma treated substrate.

In contrast, the diffusion coefficient values measured for the bilayer spanning across aqueous filled 3 μm diameter cavities 103 were determined to be 10.2±0.6 μm$^2$/s with an a value at 0.989±0.004. Furthermore, the diffusion coefficients of the bilayer 106, 107 spanning the cavities made from 5 μm spheres were determined to be D=11.2±0.4 μm$^2$/s with a at 0.992±0.002. i.e. within experimental error, they were the same. Interestingly though, the diffusion co-efficient values obtained from lipid bilayers spanning cavities made from 1 μm spheres was observed to be lower than those observed for 3 μm and 5 μm samples with D=7.1±0.3 μm$^2$/s with a at 1.012±0.004. This difference in diffusion co-efficient is possibly related to a variation in curvature of the lipid bilayer 106, 107 above a cavity 103, which will vary with cavity dimensions, causing an increase in diffusion. However, this curvature is more prominent in the larger diameter cavities i.e. 3 μm and 5 μm, and decreases for the smaller (1 μm) size cavities, leading to a decrease in the diffusion coefficients. Nonetheless, the key point is that distinctly higher diffusion co-efficient values are observed for the cavity 103 spanning bilayers 106, 107 than over the flat regions (at least 2 fold). Another explanation for this phenomena is that there is a greater contribution from lipids which have diffused over the planar region of the array contributing to the measured diffusion coefficient and these lipids are slower moving having been retarded at the planar surface—it is a key advantage of using larger pores that such lipids don't contribute.

The high lateral mobility/diffusion of lipids on the arrays 100 is attributed to the underlying aqueous environment provided by the buffer (e.g. solution 105) filled cavities 103 that effectively separates the lipid bilayer from the underlying substrate allowing it to move freely in 2-dimensions. The close resemblance of the diffusion value of the cavity spanning bilayer 106, 107 to that observed for known GUVs indicates that the lipids spread over a cavity 103 behave as free-standing vesicles owing to the aqueous reservoir formed by cavity 103 below the inner leaflet of the spanning bilayer. As the cavity depth is more than half the diameter of the cavity, e.g. 1.5 μm for the 3 μm pore, the cavity is sufficiently deep even for the smallest cavity sizes that there is little chance of protein or lipid over the pore interacting with the underlying substrate. The microcavity structure presents both planar and cavity regions in a single experiment so that both solid supported and reservoir supported lipid diffusion can be compared—the planar regions being the regions between the cavities 103 on the surface of the substrate 104.

(ii) Reconstitution of Membrane Proteins in the Spanning Bilayers.

Motivated by the fluidity of the suspended bilayers and the evident decoupling of the lipid from the substrate over the cavities, the inventors of the subject application also investigated the prospect of reconstituting membrane proteins into the cavity spanning lipid bilayers 106, 107. Again, although lipid bilayers are described, only a single lipid layer 106 may also be used.

For the investigation, the Human Glycophorin A (GpA) protein and Annexin V were used as model proteins. GpA is one of the best characterized membrane proteins and is provided as an example of a peripheral protein. In vivo, GpA is known to span the plasma membrane, with its C-terminal end at the cytoplasmic side of the membrane, a hydrophobic region penetrates through the membrane, and its N-terminal side, which is glycosylated is exposed to the exterior of the membrane. Glycophorin A was tagged with 5-Carboxytetramethylrhodamine (TAMRA). The labelled Glycophorin A was then reconstituted into vesicles. The bilayers were formed at the cavity arrays by fusion of the tagged Glycophorin A containing vesicles onto DOPC monolayers formed over 3 µm cavity substrates using LB deposition.

Glycophorin A can be reconstituted into the vesicles in a manner almost identical to that described above for the integrin, except no detergent is required and no bio-bead detergent removal. The vesicles are purified by centrifugation.

Figure 6:
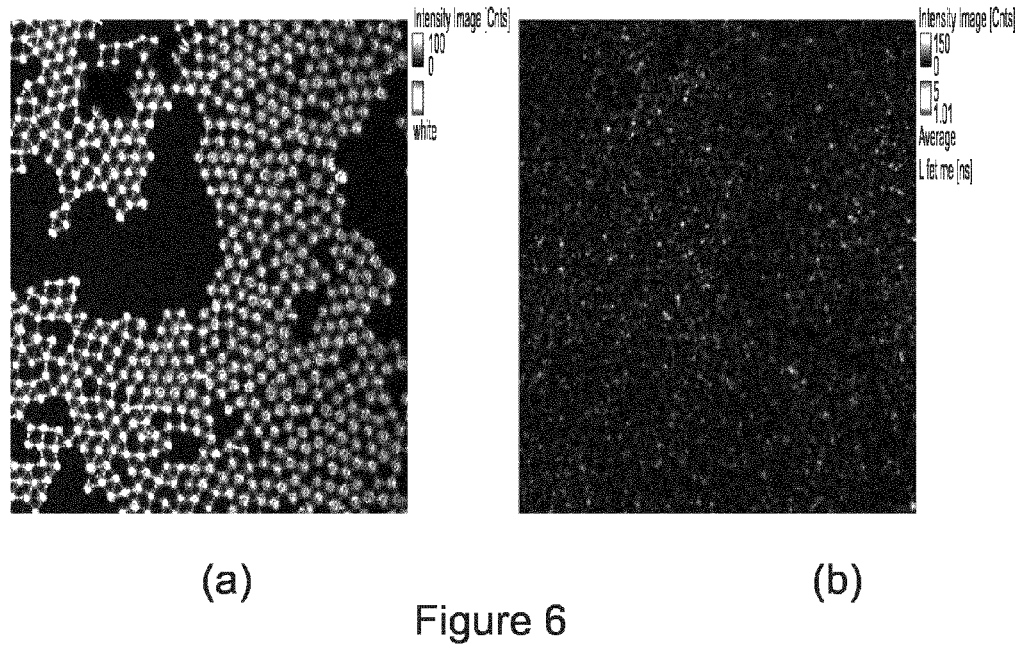
FIG. 6 shows FLIM images (a) reflectance and (b) fluorescence of Glycophorin A containing bilayer spanning a 3 µm diameter cavity.

FIG. 6 shows FLIM images (a) reflectance and (b) fluorescence of the Glycophorin containing bilayer spanning a cavity made from 3 µm sized spheres. The Glycophorin here is tagged with the fluorophore TAMRA, the excitation wavelength was 532 nm.

Figure 7:
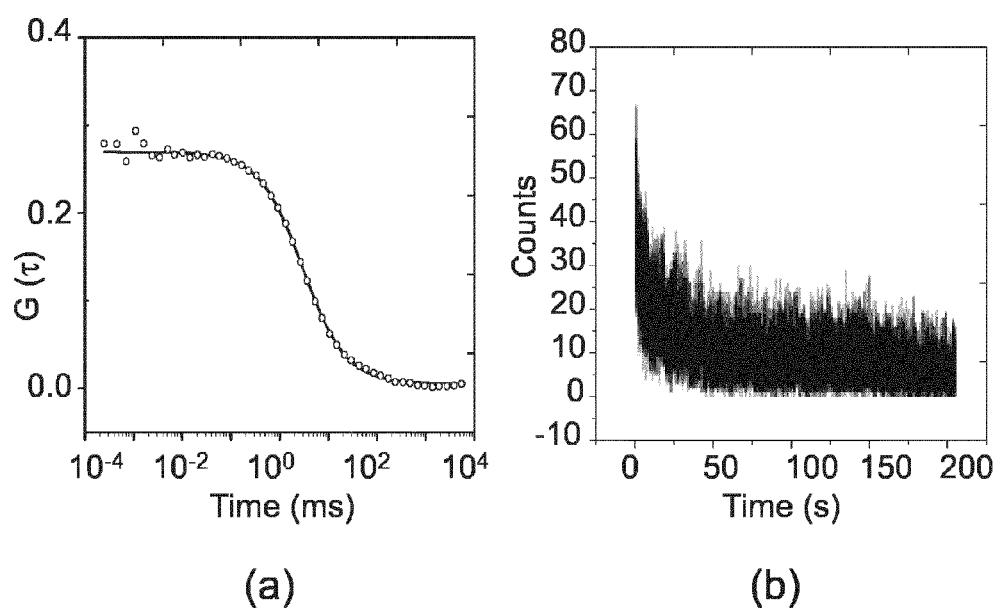
FIG. 7 shows (a) a normalized autocorrelation curve measured above a 3 µm diameter cavity (circular symbols) and (b) an Intensity-time curve for the measurement performed over flat regions on a supported lipid bilayer.

As shown in FIG. 6, the confocal fluorescence image (b) of the resulting cavity supported lipid bilayer indicates the formation of a homogenous lipid bilayer film. As the only source of fluorescence is the TAMRA labelled Glycophorin A Image (b) indicates that the Glycophorin A was well incorporated within the bilayer. Consistent with its incorporation into the bilayer, the Glycophorin A was found to be essentially immobile over the planar regions of the cavities reflected in the photobleaching in the intensity-time curve in FIG. 7b obtained by FLCS measurements. This result is consistent with what would be expected on a lipid bilayer supported on a planar substrate and is attributed to the interaction of the cytoplasmic tail of the protein with the underlying PDMS in the planar regions of the array leading to a loss of lateral mobility. Conversely, GpA was found to be mobile over the cavities and the diffusion coefficient of the GpA over cavity were measured by FLCS to be $7.1\pm0.6$ µm$^2$/s with a of $0.992\pm0.005$, obtained by fitting the autocorrelation curve in FIG. 7a using equation 1. This value compares remarkably well with the diffusion coefficient for GpA in a free standing DMPC liposome above its phase transition temperature ($D_{GpA}=(4\pm2)\times$µm$^2$/s at 30° C.) using Fluorescence Recovery after Photobleaching (FRAP). Consistent with the lipid diffusion values over the cavities, the close match of diffusion rate for a membrane protein at the cavity and in a liposome is good evidence that the protein experiences little or no frictional interaction with the surface over a spanning cavity.

Figure 8:
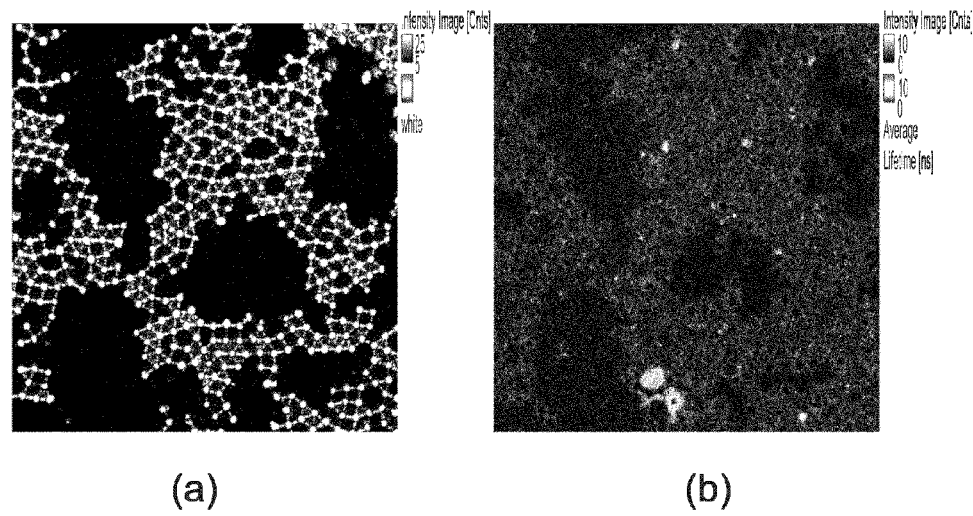
FIG. 8 shows FLIM images (a) reflectance and (b) fluorescence of labelled Annexin V containing bilayer spanning a 3 µm diameter cavity.

To demonstrate the extension of a system provided in accordance with the present teaching to multiple protein types, a transmembrane protein Annexin V was also studied using the platform of FIG. 1. FIG. 8 (a) shows a reflectance image of the PDMS substrate 104 which allows for the location of buffer filled cavities. This allows for the identification of points where FLCS should be performed. Figure (b) shows an image of Annexin V labelled with Atto 647N in a lipid bilayer (80% DOPC, 20% DOPS) above the cavities shown in FIG. 8(a). FLCS point measurements were performed on the labelled protein on both planar PDMS and above cavities based on the reflectance of image (a). Both images (a) and (n) are 80×80 µm.

Figure 9:
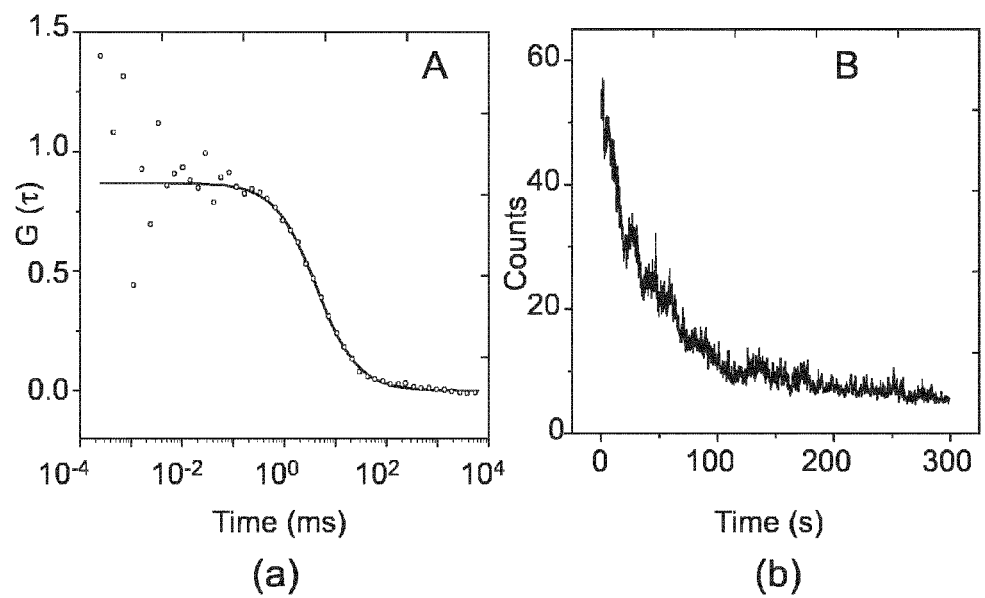
FIG. 9 shows (a) a normalized autocorrelation curve measured above a 3 µm spanning cavity (red circular symbols) and (b) an intensity-time curve for the measurement performed over flat regions on the supported lipid bilayer.

FIG. 9(a) shows a normalized autocorrelation curves measured above a 3 µm spanning cavity (circular symbols). FIG. 9(b) shows an intensity-time curve for the measurement performed over flat regions on the supported lipid bilayer. In both measurements, the fluorophore observed is Annexin V tagged with Atto647. Measurements were performed over 200 s.

The diffusion co-efficient and mobile fraction of Annexin V in this cushioned lipid bilayer system varied depending on polymer size and concentrations. For example: In a single cushion system of 0.5 mol % PEG 5000, a diffusion co-efficient of 3.5 µm$^2$/s was observed where $24.6\pm1.7$% of the Annexin molecules were mobile. Using a double cushioned system of 0.5 mol % PEG 5000 and BSA, a diffusion co-efficient of $2.9\pm0.4$ µm$^2$/s was observed where $73.5\pm2.4$% of the Annexin was mobile. Of particular note is the fact that, a large percentage of the labelled protein was immobile, and thus the diffusion values were obtained from the mobile fraction. The same protein immobility on planar PDMS was observed where a significant degree of bleaching was also observed. Crucially however, the use of the microcavities 103 in the present teachings prevents non-specific interaction between protein and underlying substrate 104. Over these cavities no bleaching is observed and the Annexin V protein diffuses freely with a diffusion co-efficient close to that of lipid.

The results of the investigations described above with reference to FIGS. 3-8 clearly demonstrates that an array 100 provided in accordance with the present teaching offers significant advantages for studying the mobility for both lipids and transmembrane proteins. They exhibit the fluidity of a liposome, due to the efficient decoupling of the inner leaflet of the layer 106 or bilayer 106, 107 from the substrate 104 with the versatility and stability of a supported lipid layer 106 or bilayer 106, 107. These structures have a number of key applications in biophysics.

Although described above with regard to PDMS only, the arrays can also be prepared in metal either by direct electrochemical deposition or vapour deposition over the PDMS arrays, or by direct electrochemical/vapour deposition around the polystyrene spheres.

In using metal arrays electrochemical as well as fluorescence other spectroscopic measurements (e.g. Fluorescence lifetime correlation spectroscopy, Raman spectroscopy) can be used. The inventors have demonstrated voltammetry and in particular Electrochemical Impedance Spectroscopy (EIS) of the arrays. As an example:

A gold microcavity electrode is first modified with 2-mercaptoethanol by immersing them in a 1 mM solution in ethanol overnight after which they are sonicated in Tris buffer for 30 munities to pre fill the cavities (in the gold electrode or substrate). A DOPC monolayer is then deposited onto the microcavity electrode using a Langmuir-Blödgett deposition of monolayer followed by DOPC disruption at this monolayer to form a bilayer.

Measurements are performed with a potential of 0 V and a frequency range of 0.01 Hz to 100000 Hz with a standard 3 electrode set up with an Ag/AgCl reference electrode. All experiments are performed in Tris NaCl buffer with the cell contained inside a Faraday cage.

Figure 10:
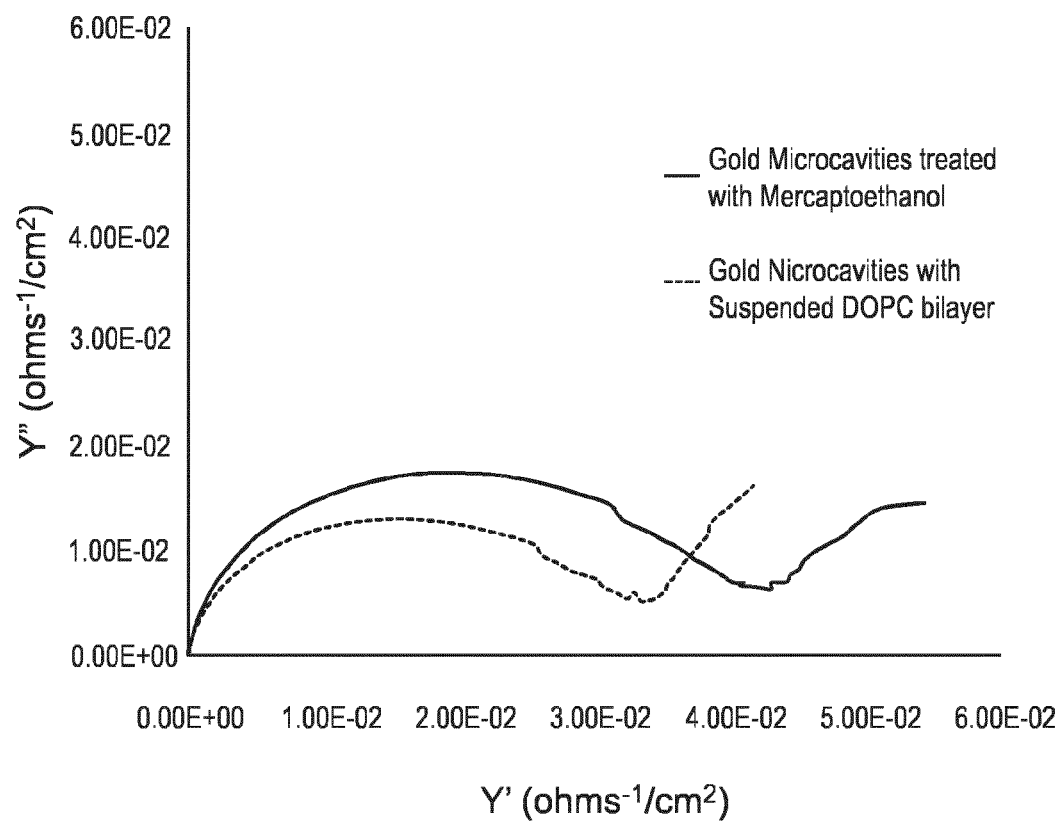
FIG. 10 is an admittance plot of 5 micron diameter gold microcavity array electrode, treated with mercaptoethanol, before and after DOPC bilayer formation.

The admittance plot of FIG. 10 shows a clear decrease in the admittance after the formation of the DOPC bilayer onto the mercaptoethanol treated gold microcavity array (electrode). In FIG. 10, an admittance plot of 5 micron diameter gold microcavity array electrode, treated with mercaptoethanol, before (top curve) and after DOPC bilayer formation (bottom curve). Measurements are performed in Tris buffer, using a standard 3 electrode set up at 0V (Vs Ag/AgCl) using a frequency range of 100000 Hz to 0.01 Hz.

Admittance is directly proportional to capacitance (C), which can then be related to the thickness of the membrane on the micro-cavity electrode using the following equation:

$$C = \varepsilon\varepsilon_0 \frac{A}{d}$$

Where ε is the dielectric constant of the membrane, $\varepsilon_0$ is the permittivity of vacuum, A is the area of the microcavity electrode and d is the thickness of the membrane. This equation shows that capacitance is inversely proportional to membrane thickness. Therefore the decrease in the admittance observed after bilayer formation corresponds to an increase in the thickness of the membrane on the electrode due to the addition of the DOPC bilayer onto the mercaptoethanol treated microcavity electrode.

Electrochemical Impedance Spectroscopy (EIS) is highly sensitive to changes in the bilayer and this sensitivity can be enhanced by using an electrochemical probe such as ferrocyanide in the contacting solution (i.e., solution contacting the outer surface of the array) or in applying an ionic gradient across the membrane by applying slightly different pH or ionic strength at the solution at each side of the membrane e.g., by pre-filling the cavities with a different ionic strength solution to that contacting solution which will operably be in contact with the top leaflet of the bilayer (i.e. away from the cavity). Within this context the inner membrane leaflet refers to the lipid layer closest to the cavities and the outer leaflet is that the lipid layer pointed away from the cavities and operably in contact with the contacting solution that is introduced into the inlet and out through the outlet of the microfluidic platform.

Figure 11:
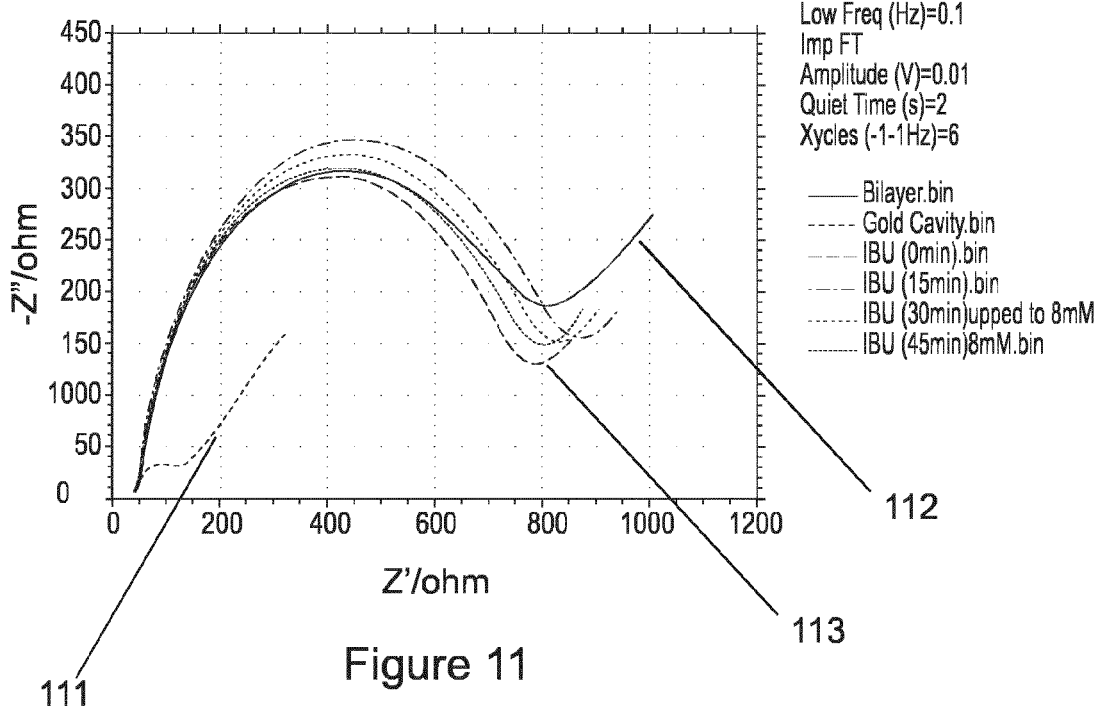
FIG. 11 is an admittance plot of the effect of introduction of ibuprofen (4 mMol) to DOPC bilayer at 2.8 um gold cavity arrays on the AC impedance spectroscopy of the bilayer.

EIS at the array has application in drug-membrane interactions. FIG. 11 is an admittance plot showing the effect of introduction of ibuprofen (4 mMol) to a DOPC bilayer at 2.8 μm gold cavity arrays on the AC impedance spectroscopy of the bilayer. The experiment was carried out in PBS buffer at pH 7.4 at room temperature with cavities filled with same buffer solution. A microfluidic platform having an inlet and outlet (similar to the platform of FIG. 2) is used to introduce the ibuprofen to the bilayer.

Line 111 of FIG. 11 shows the impedance of the arrays without the bilayers, line 112 shows the impedance with a DOPC bilayer alone and the remaining lines show the result on exposure to ibuprofen at 4 and then 8 mMol over varying times. $(Fe(CN)_6)^{-4/-3}$ ferrocyanide was used as a redox probe, though it is not necessary to use same to elicit a useful analytical response. Application of the ibuprofen through the microfluidic platform results initially in a decrease followed by a substantial increase in capacitance of the layer. It is clear that the response takes several minutes to reach equilibrium at which point the ibuprofen causes a decrease in impedance; attributed to modest disruption of the bilayer structure (i.e. it is more porous).

Figure 12:
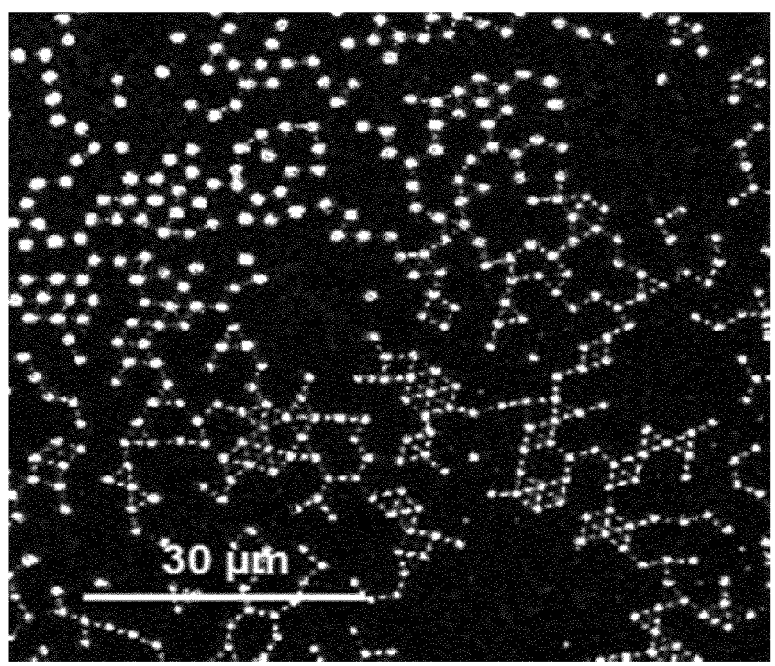
FIG. 12 (A) is a fluorescence lifetime image of the 2.8 um diameter pores in PDMS following addition of ibuprofen (4 mMol) to a DOPC bilayer.
Figure 12:
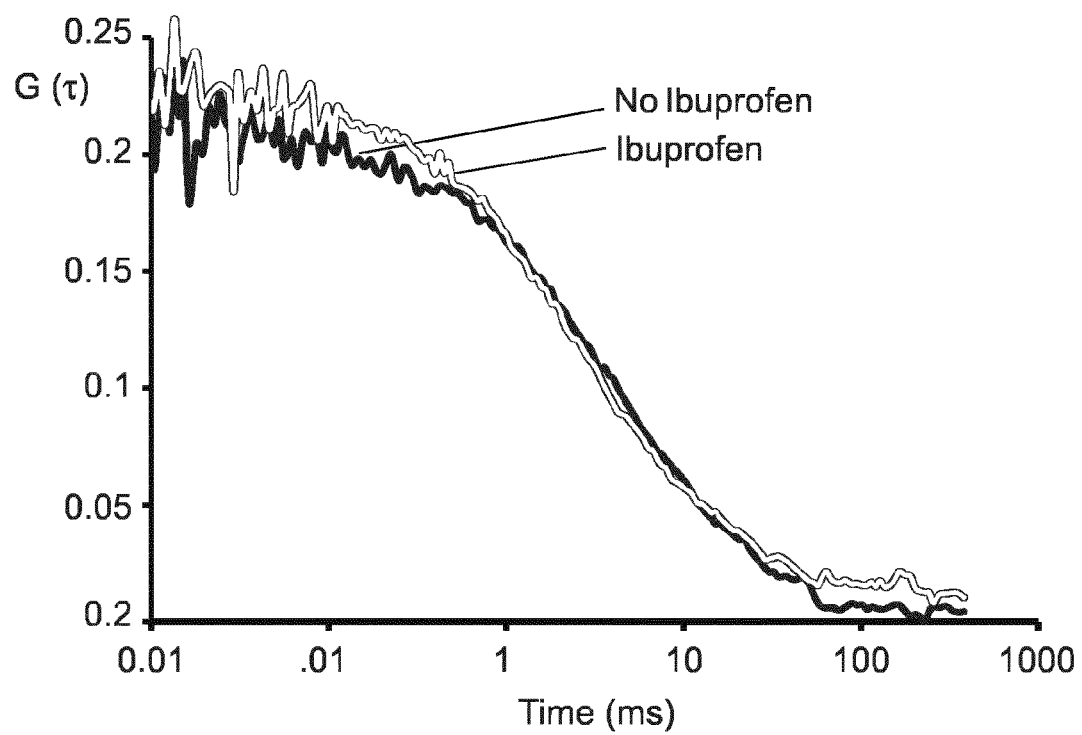

Correspondingly, exposure of the bilayer to ibuprofen results in increases in the membrane lipid diffusion coefficient from approximately 7 to approximately 9.5 $\mu ms^{-1}$ reflected in FLCS. FIG. 12 (A) which provides a fluorescence lifetime image of the 2.8 um diameter pores in PDMS following addition of ibuprofin (4 mMol) to the DOPC bilayer as carried out in PBS buffer at pH 7.4 at room temperature. The probe is BODIPY labelled DOPE at 1% mol/mol lipid. FIG. 12(B) shows the autocorrelation function from FLCS of these same arrays reflecting the changes to the dynamics of diffusion of the lipid on introduction of ibuprofen.

In accordance with the present teachings a novel approach to the design of a free-spanning lipid layers (and bilayers) has been described. The lipid layer 106 or bilayer 106, 107 is fabricated over aqueous buffer-filled micro-cavities on polydimethoxysilane (PDMS) substrates using Langmuir Blodgett monolayer assembly followed by fusion with small uni-lamellar vesicles to form an array. Furthermore, the array 100 can be assembled into a simple microfluidic chamber such that it can be directly mounted onto microscope stage. Using Fluorescence Lifetime Correlation Spectroscopy (FLCS) it can be demonstrated that the lipid layer or bilayer suspended over a cavity is highly fluid exhibiting diffusion coefficients comparable to free-standing vesicles in solution.

Furthermore, one of the biggest unresolved challenges in working with membrane proteins in artificial lipid bilayers is overcome in the system of the present teachings. Specifically, unhindered diffusion of the protein in the supported layer i.e., lipid layer/bilayer is achieved. As a result of its cell-like environment presenting aqueous reservoirs on both sides of the lipid layer or bilayer, membrane proteins incorporated into the layer(s) achieve full lateral mobility with no coupling to the underlying substrate. This is exemplified by the above outlined study of two membrane proteins reconstituted into the bilayer with different dimensions in their extracellular and cytoplasmic domains—Glycophorin A and Annexin V. In both cases, once over the cavity both proteins showed 100% mobility. It has also been demonstrated for integrin protein αIIbβIII An additional key advantage of these arrays is that they do not require use of organic solvent in the lipid layer/bilayer preparation. They are stable and amenable to incorporation into a microfluidic format. Overall, these array open up opportunities to study transmembrane proteins in biomimetic environment decoupled from the complexity of the cell membrane whilst exhibiting liposome-like fluidity with much greater stability and versatility.

Using an array per the present teaching it is possible to investigate and analyse a number of different drug membrane interactions. As an example of the efficacy of this approach three examples will be discussed below:

(a) By Fluorescence Monitoring Modulation of Lipid Dynamics in the Bilayer Caused by Drug-Membrane Interaction Using a Fluorescently Labelled Bilayer at the Cavity Array.

Figure 13:
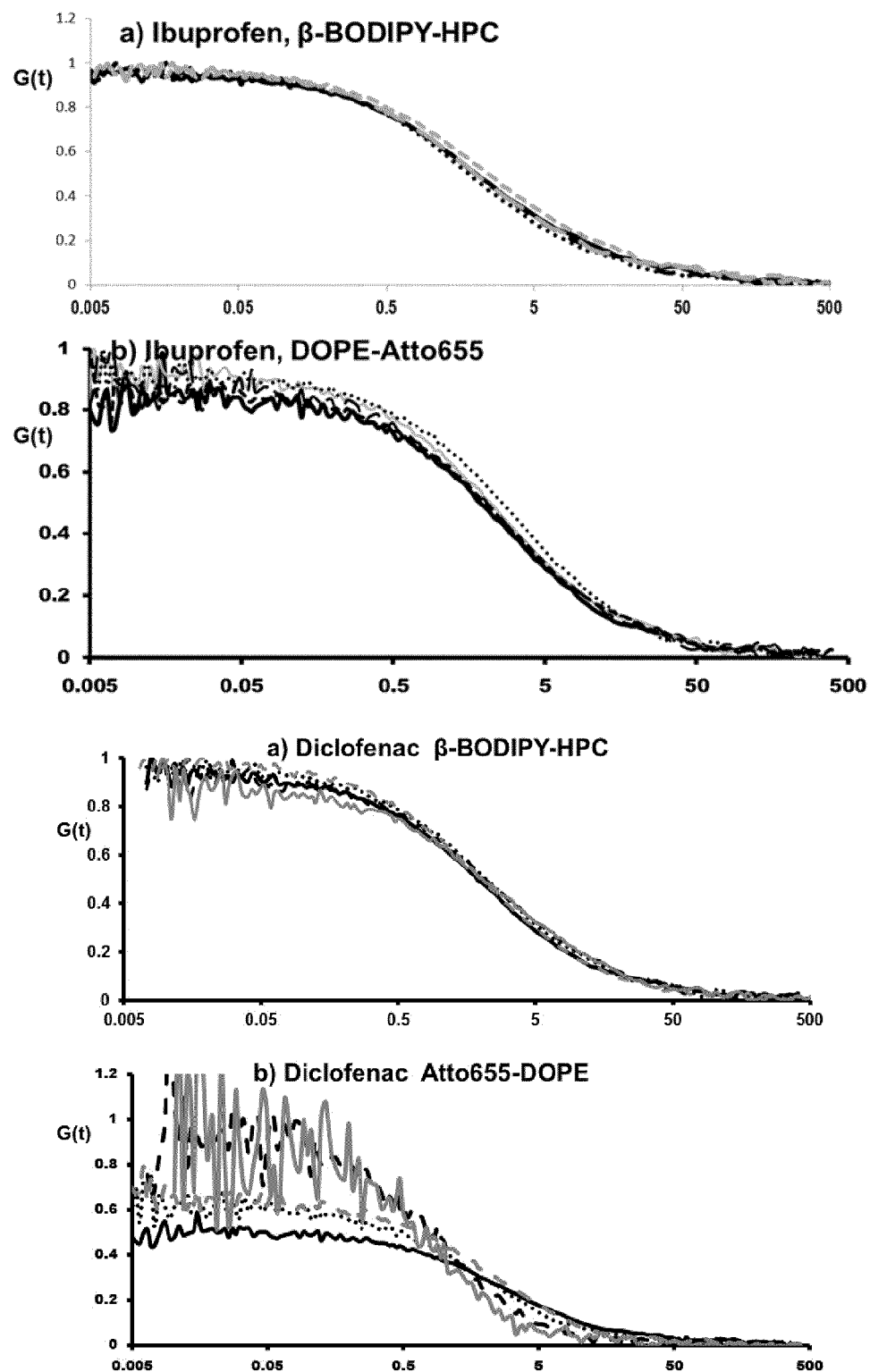
FIG. 13 demonstrates experimental data showing autocorrelation functions for specified experimental data.

An example study is the interaction of nonsteroidal anti-inflammatory drugs (NSAIDs) Diclofenac and Ibuprofen with lipid membrane models; FIG. 13 demonstrates Autocorrelation functions (ACFs) from PBS filled 2.8 um diameter PDMS pores supporting a DOPC lipid bilayer Labelled with 1 mol/mol DOPElabelled BODIPY-HPC labelled) without and then following incubation (15 mins) of 4, 20, 100 and 200 μmol with the bilayer (B) with 1 mol/mol labelled DOPE-ATTO655 labelled) without and then following incubation (15 mins) of 4, 20, 100 and 200 μmol ibuprofen (c) Labelled with 1 mol/mol labelled BODIPY-HPC labelled) without and then following incubation (15 mins) of 4, 100, 400 and 800 μmol of diclofenac with the bilayer (B) 1% mol/mol labelled DOPE-ATTO655 labelled bilayer without and then following incubation of 4, 100, 400 and 800 μmol of diclofenac. The bilayers were in contact with PBS buffer pH 7.4.

This shows the influence of the NSAIDs over several concentrations on the diffusion dynamics of labelled lipid bilayer (1% mol/mol labelled DOPE-ATTO655 in DOPC bilayers over cavities. Two labelling regimes were explored; DOPE labelled with ATTO 655; which is a hydrophilic probe attached at the hydrophilic phospholipid headgroup and sits at the external aqueous interface of the bilayer and BODIPY-HPC; 2-(4,4-difluoro-5-methyl-4-bora-3a,4a-diaza-s-indacene-3-dodecanoyl)-1-hexadecanoyl-sn-glycero-3-phosphocholine, i.e. wherein the lipophilic BODIPY is bound onto the terminus of the oriented toward the interior of the bilayer. Monitoring the diffusion of each probe permitted assessment of interaction of the drug with the membrane and where this interactions occurred; i.e. did it bind to the interface or intercalate in the bilayer? Only a single probe is necessary in most instances, however depending on the sophistication of the FCS instrument two labels can be used in a single two colour experiment or they can be applied in separate experiments to yield detailed insights into the location of the drug at the membrane.

The ACFs for diclofenac and ibuprofen responded differently with each probe. Whereas ibuprofen had, within experimental error, little impact on the diffusion of the lipophilic BODIPY-HPC probe, it exerted a significant impact on the diffusion of the ATTO probe, the diffusion coefficient increased from $10.37\pm0.72$ $\mu m^2$ $s^{-1}$ to $12.05\pm0.6$ $\mu m^2$ $s^{-1}$ on introduction of 100 μmol of ibuprofen to the lipid array.

Similarly, diclofenac had little effect on the diffusion of the BODIPY-HPC probe however, it induced large systematic increases in the diffusion coefficient of Atto-655 labelled DOPE which rose from $11.71\pm0.82$ $\mu m^2$ $s^{-1}$ to $43.5\pm8.13$ $\mu m^2$ $s^{-1}$ on increasing concentration of diclofenac from 0 to a concentration of 800 μmol.

The lack of significant change to the internally oriented probe and large (particularly for diclofenac) change in diffusion of the hydrophilic probes suggests that the drugs do not intercalate strongly into the membrane. Rather it indicates that both drugs bind at the aqueous interface. The very large change in the diffusion coefficient of the ATTO-DOPE indicates that there is a strong interaction of the drug with this probe which may pull the probe away from the lipid interface. Such behaviour has been seen previously for PEG modified bilayers and the results are consistent with what is known about these NSAIDs, and observations noted by Brandenberg et al, (The membrane-activity of Ibuprofen, Diclofenac, and Naproxen: A physico-chemical study with lecithin phospholipids Marcela Manrique Moreno, Patrick Garidel, Mario Suwalsky, Jorg Howe, Klaus Brandenburg, Biochimica et Biophysica Acta (BBA)—Biomembranes 1788, 2009, Pages 1296-1303) who showed from IR and calorimetric studies of Diclofenac and Ibuprofen with liposomes that they are lipid membrane surface binding but non-intercalating. Furthermore, using the arrays with fluorescence correlation spectroscopy it is possible per the present teaching to follow equilibrium binding to the bilayers by monitoring to obtain quantitative binding information.

(b) Using Gold Arrays Both Fluorescence and EIS can be Used to Study Drug-Membrane Interactions or EIS on Gold Arrays Alone is Very Sensitive to Structural Changes in the Bilayer Induced by Drug Partitioning into or Association with the Layer and can be Used to Study these Processes Dynamically.

Figure 14:
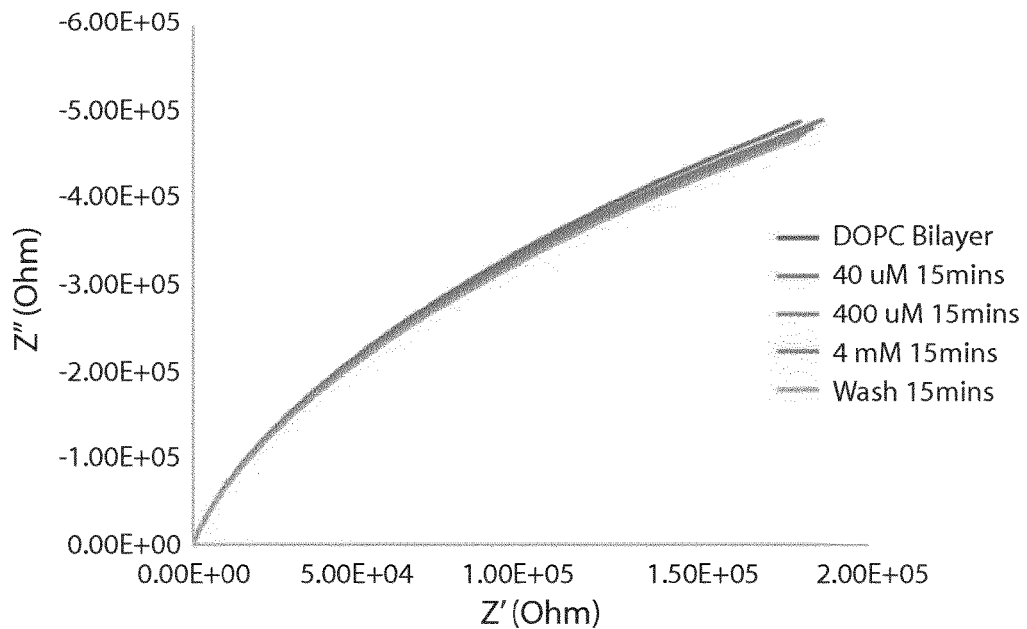
FIG. 14 shows Electrochemical Impedance Spectra (EIS) of a DOPC bilayer supported across aqueous phosphate buffered saline (PBS) solution
Figure 14:
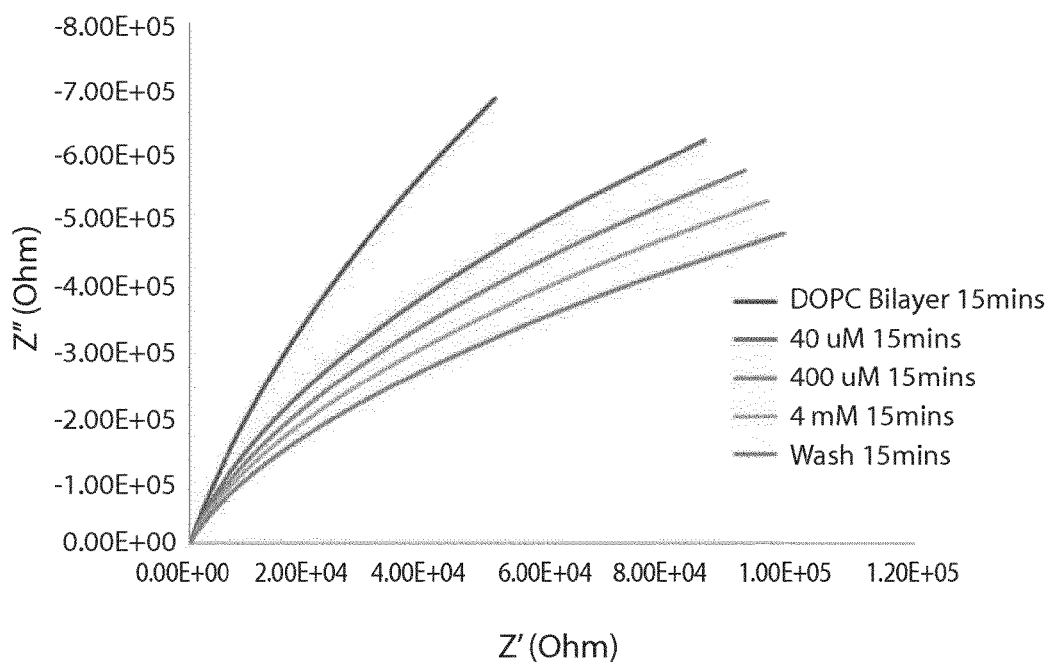

Electrochemical Impedance; In studies parallel to the diffusion studies on NSAIDS FIG. 14 shows the impact of the same drug concentration range on the impedance of DOPC bilayer (the bilayers were in contact with PBS buffer pH 7.4 on both sides of the pore) The interaction of both NSAID results in a reduction in the resistance of the bilayer. The magnitude of the change across each drug is considerably different with roughly 6% ($\pm2\%$) decrease in resistivity for ibuprofen between the 0 and 400 umol compared with 65% ($\pm4\%$) decrease for diclofenac. These results, particularly in the context of the magnitude of the influence of the drug on the membrane are consistent with those of FLCS. Electrostatic binding of the drug to the membrane reproducibly decreases the impedance response at the bilayer. The bilayers are stable to introduction of several volumes of buffer at the end of a study and we were able to monitor for reversibility of binding. Washing the bilayer through with 6 volumes of drug free buffer partially recovered the bilayer resistance. A control experiment confirmed that such washing has no influence on a bilayer which had not been treated with drug.

The results from EIS, in terms of magnitude of response and reproducibility are further improved by selectively modifying only the top layer of the gold array with a more closely packed long chain alcohol e.g. mercaptoehexanol to ensure the only electrochemically responsive area is the pore. This approach also simplifies the impedance model that is used. This has been demonstrated in investigation of galectins in asymmetric GM1 DOPC/Chol lipid bilayers and in ion channel (gramicidin and antiporter nigercin) containing DOPC bilayers.

For comparison; an example of the effect of a strongly partitioning drug the antibiotic Rifampicin was examined. EIS studies of the addition of this drug over concentration range 0 to 100 umol to the gold cavity supported bilayer described above demonstrates very large decreases in film resistance from the EIS signal, shown in FIG. 15. The lower concentration range reflects therapeutic concentration ranges.

The far greater magnitude of EIS changes for lipid bilayer assembled across buffer filled cavity arrays compared to the NSAIDs reflect the fact that this lipophilic drug partitions into and crosses over the bilayer, thereby perturbing the bilayer structure and reducing film resistance. Correspondingly, the diffusion coefficient of the DOPE-Atto655 labelled DOPC layer was dramatically increased by the presence of rifampicin. Furthermore partitioning was essentially irreversible, with little or no recovery of impedance after washing the film. In a control experiment washing the DOPC layer in the same way in absence of Rifampicin does not significantly affect impedance.

Figure 15:
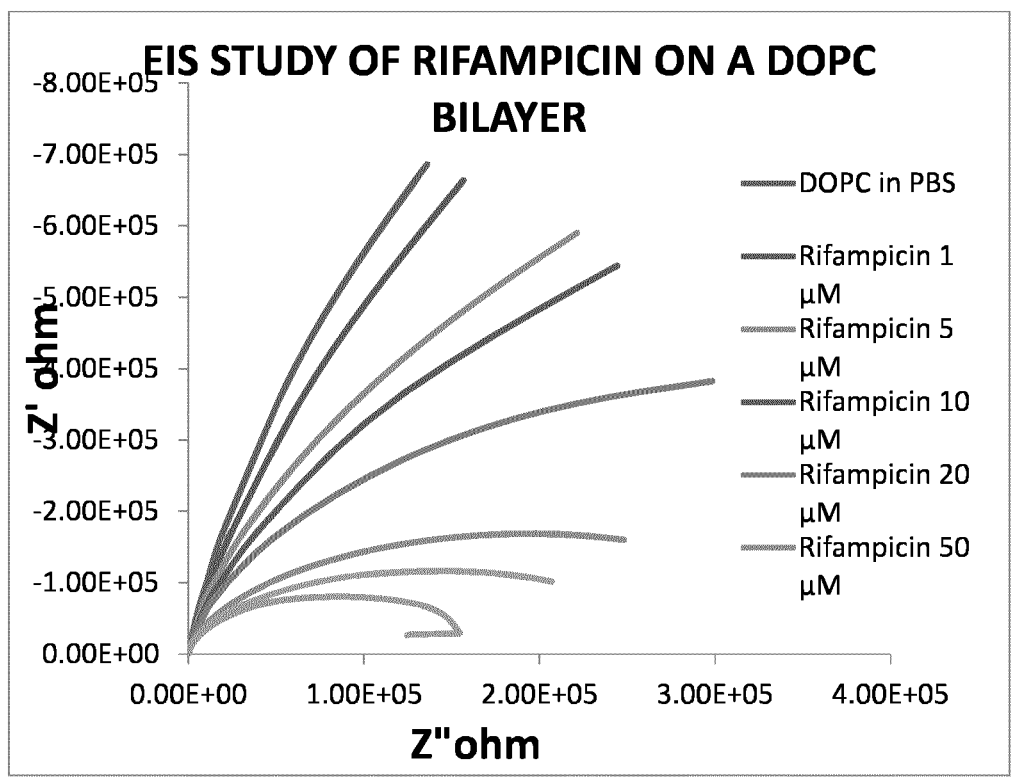
FIG. 15 shows results from an; EIS study of Rifampicin at a gold cavity supported DOPC bilayer, following introduction of 0 to 100 umol drug into the flow channel of the array in contact with PBS buffer.
Figure 16:
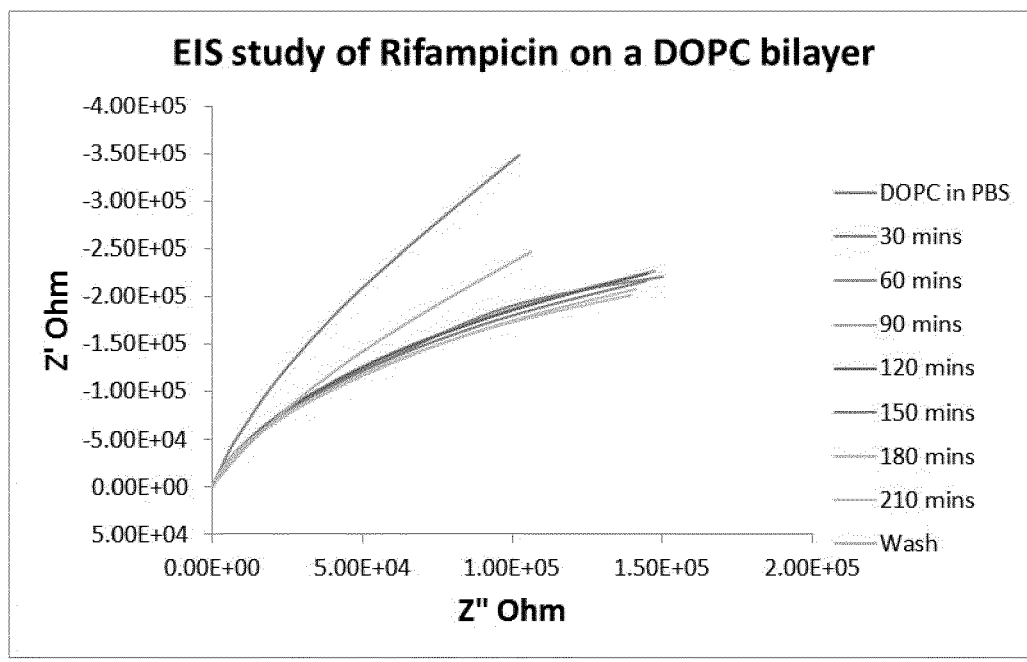
FIG. 16 shows results from an EIS study of Rifampicin at a gold cavity supported DOPC bilayer, following introduction of 10 umol drug into the flow channel of the array in contact with the bilayer. This experiment was carried out in the dark to avoid light induced Rifampcin reactions. The chamber was left overnight in the dark and showed no further change.

A system array per the present teaching also permits dynamic studies of the effect of drug on the bilayer where in the example of Rifampicin it was found that the drug took approximately 30 minutes to partition into the layer and also revealed that partitioning was largely irreversible, as demonstrated by the washing step in FIG. 15. In the example of FIG. 15, the stability study of Rifampicin (10 μM) was carried out in the presence of light. The resistance of the bilayer is decreasing over a period of time. The decrease of the resistance is due to the drug changing form over a period. FIG. 16 shows an example of stability study of Rifampicin (10 μM) in contact with DOPC bilayer and confirms that the drug equilibrates with the bilayer in less than 30 minutes and the response is then stable. At lower concentrations of drug some recovery of the EIS response was obtained on washing. EIS response became irreversible at high drug concentrations (>60 umol).

Figure 17:
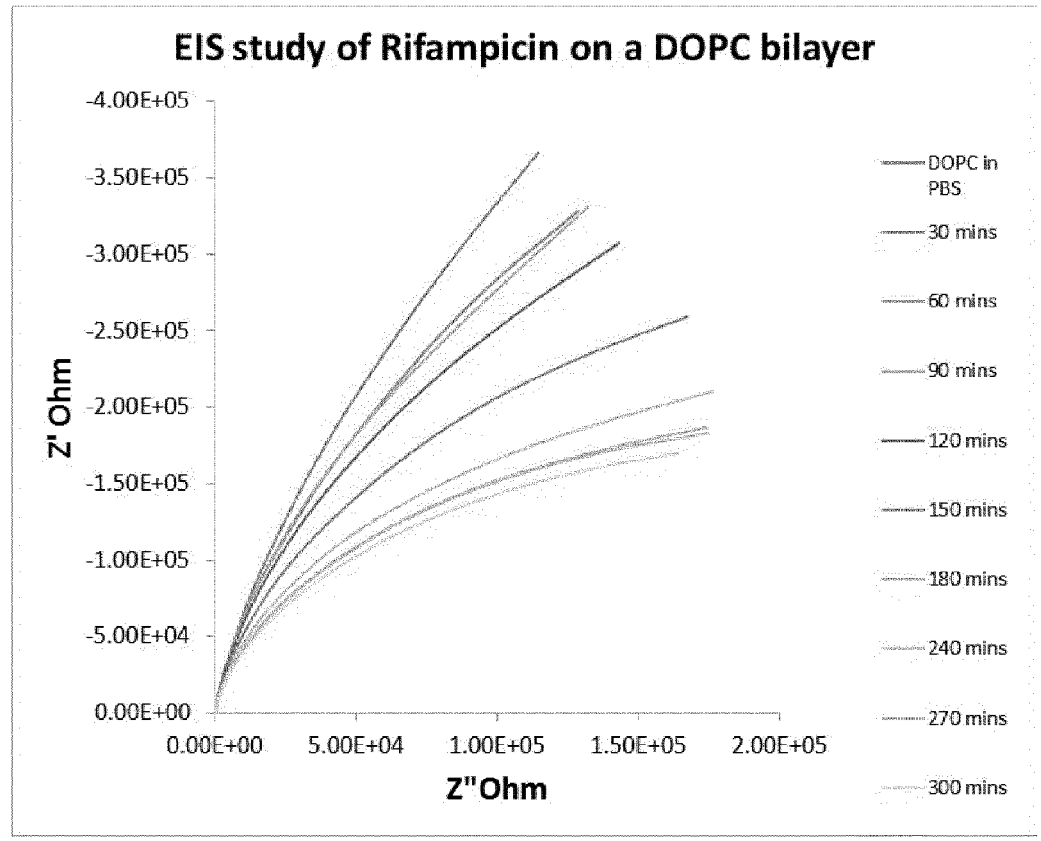
FIG. 17 shows an EIS study of Rifampicin at a gold cavity supported DOPC bilayer, following introduction of 10 umol drug into the flow channel of the array in contact with the bilayer; the experiment was carried out under illumination and time dependent impedance change reflects the photoredox reaction of Rifampicin.

Furthermore, as exemplified with reference to the data in FIG. 17 an array per the present teaching can be used to follow reactions, for example stability studies whilst the drug is partitioned into the bilayer.

In this example the light induced oxidation of Rifampicin was followed whilst it was at a DOPC bilayer and these redox changes were reflected in decreasing resistance over time. In the absence of light the impedance signal was stable overnight.

c) The Gold Arrays can be Used to Enhance Spectroscopic Studies, Particularly Raman Studies of Probe-Bilayer Interactions and to Detect Crossing of a Drug into the Cavity Interior.

An example of the application of arrays provided in accordance with the present teaching as a model for transporter molecules is the application of ionophores responsible for transporting small ions across the cell membrane. It will be appreciated that there are three main classifications of ionophores: uniporters, which transport a single ion across the membrane; antiporters, which exchanges one ion for another; and symporters, which transport two different ions across the membrane simultaneously.

Using an array per the present teaching, the present inventors have demonstrated an application for transporter molecules with two ionophores: Valinomycin and Nigericin. Valinomycin is a naturally occurring uniporter ionophore, which is known to spontaneously embed into lipid bilayers where it transports K+ ions across the lipid membrane. Nigericin is an antibiotic derived from *Streptomyces hygroscopicus*. Like Valinomycin it spontaneously incorporates into lipid bilayers and transports K+ ions across the lipid bilayer in exchange for H+ ions.

Gold microcavity electrodes were formed through the method described herein using electrodeposition of gold through a close packed array of polystyrene spheres (2.88 micron in diameter) after which the spheres where removed by sonication in THF for 30 minutes. The gold microcavity array was then modified with mercaptoethanol (ME) by placing the substrate in a 1 mM solution of ME, in ethanol, for 24 hours. Alternatively it is possible to selectively modify the top surface with mercaptonexanol before removal of the spheres and leave the cavities free of surface modification after sphere removal. This latter approach gives even greater reproducibility.

Figure 18:
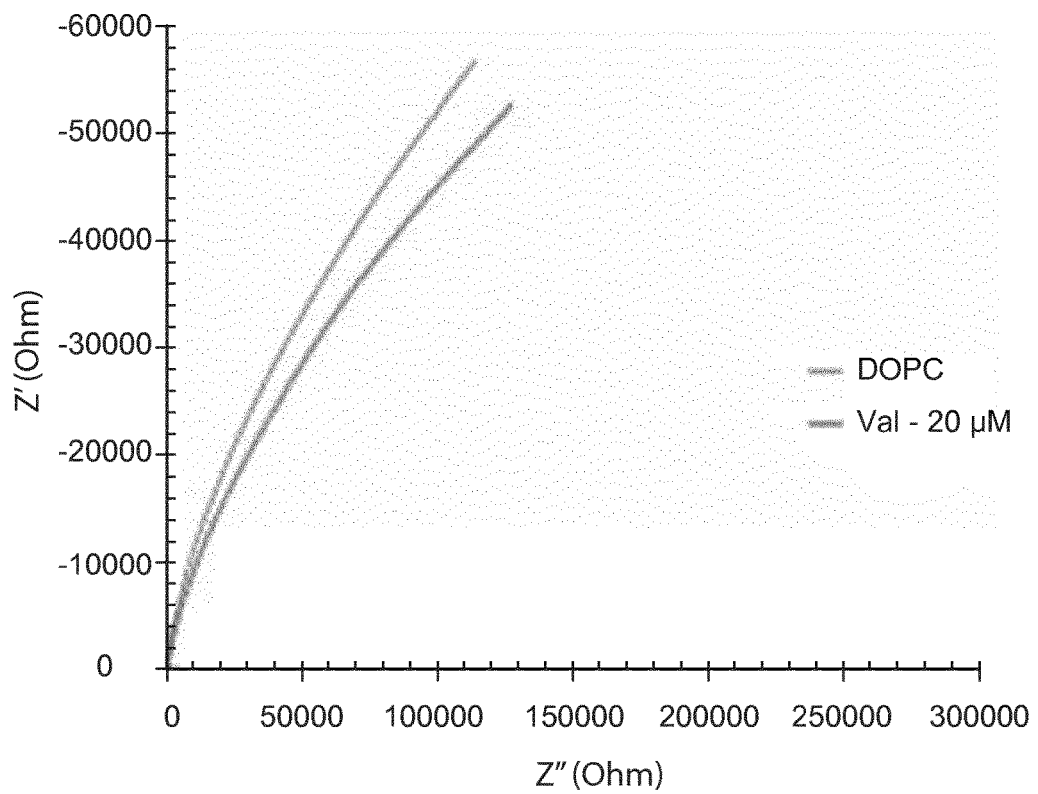
FIG. 18 shows data of use of an array per the present teaching in an application for transporter molecules with the ionophore Valinomycin.
Figure 18:
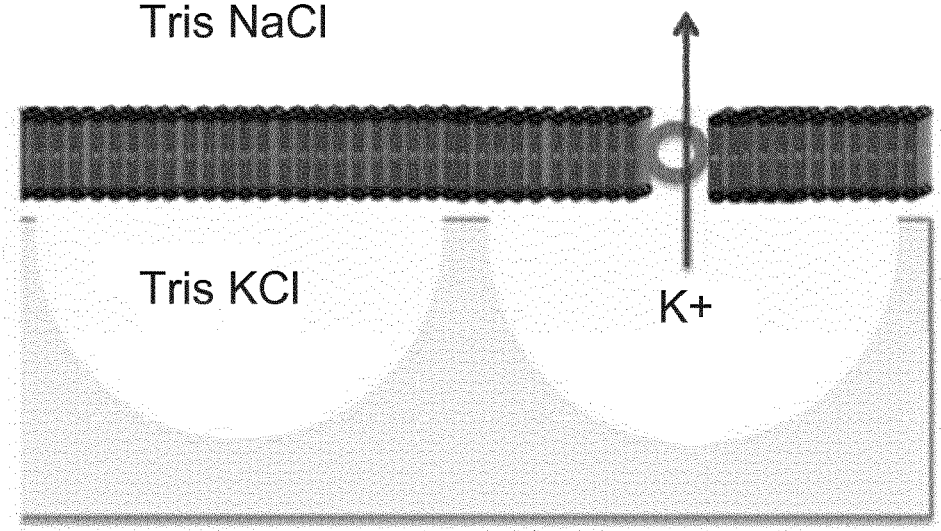

As shown in FIG. 18, for Valinomycin; the microcavities were prefilled with Tris KCl via sonication for 30 minutes prior to assembly of the bilayer. After sonication a DOPC bilayer was formed over the micro-cavities using a combination of Langmuir-Blodgett and vesicle fusion as described above.

Electrochemical impedance spectra (EIS) of this bilayer were measured by placing the array in contact with Tris NaCl. This creates an ion gradient across the lipid bilayer. The bilayer, effectively insulates the pore from the external contacting solution but once Valinomycin is introduced this should cause K+ ions to flow from inside the cavities into the bulk solution (see schematic in FIG. 18). The impedance of the DOPC bilayer was measured in the presence of this ionic gradient. Valinomycin was then introduced into the cell by adding 20 µM from an ethanol solution. The impedance of the bilayer was then measured again and a decrease in the resistance was observed (see data in the graph of FIG. 18 which is an EIS plot of the DOPC bilayers before, the line to the left—closest to the Y axis and after—the line to the right closest to the X axis, Valinomycin incorporation demonstrating the decrease in resistance observed after incorporation of the Valinomycin). Although the absolute impedance varied from sample to sample, the magnitude of the change which varies with Valinomycin concentration was reproducible. The observed decrease in resistance is due to the transport of K+ ions across the lipid bilayer by the incorporated Valinomycin.

Figure 19:
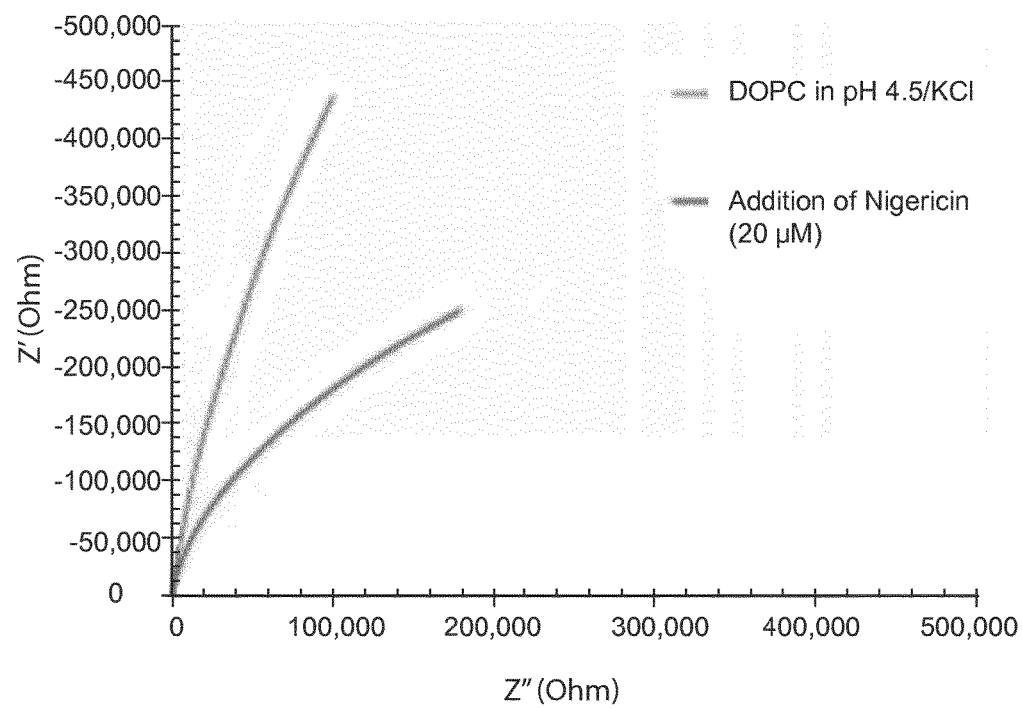
FIG. 19 shows data of use of an array per the present teaching in an application for transporter molecules with the ionophore Nigericin
Figure 19:
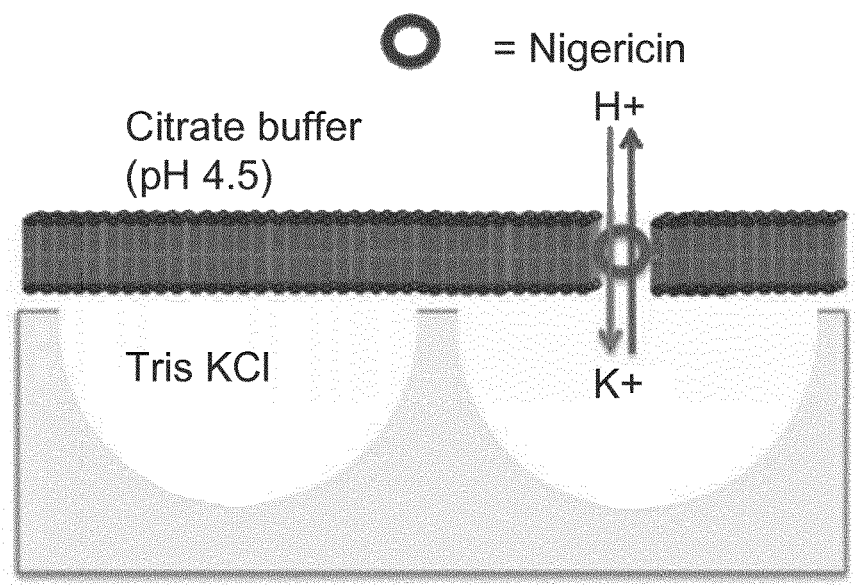

FIG. 19 shows similar data related to impedance changes in DOPC bilayers exposed to Nigericin. Nigericin is an antiporter of H+ and K+, Herein, the cavities where prefilled with 150 mM K+ before bilayer formation. Citrate buffer (at pH 4) was then added to the electrolyte to supply the system with H+(10 mMol) ions on the outside of the bilayer. The impedance of the DOPC bilayer was measured in the presence of this ionic gradient. Nigericin was then introduced into the cell by adding 20 µM of the ionophore from an ethanol solution (a control experiment was carried out which revealed that the ethanol addition to the layer at this volume had negligible effect on the impedance in the absence of Nigericin. The impedance of the bilayer was then measured again and a decrease in the resistance was observed. This decrease in resistance is due to the transport of K+ and H+ ions across the lipid bilayer by the incorporated Nigericin.

The impedance response varied with substrate but relative magnitude of the resistance decrease which was Nigericin concentration dependent showed good reproducibility (<±5%). The magnitude of the overall response and stability of response can be improved by selective modification of the top surface with long-chain thio alcohol or acid.

The truncated sphere cavities per the present teaching may also be used for controlled release of a reagent to a material immobilized in the lipid bilayer. This method can be used for the controlled/timed release of a range of reagents asymmetrically to the bilayer or for example of protein agonists to proteins within the bilayer and provides a method for addressing intercellular and extracellular binding sites on the same system.

As an example. Mercaptoferrocene was self-assembled only at the inner cavity surface and a blocking thiolated alcohol (mercaptoethanol or mercaptohexanol) was assembled at the top surface of the array, by modification of the top surface of the array prior to release of the templating sphere and then adhering the ferrocene after sphere removal. The ferrocene binds selectively to streptavidin modified beta-cyclodextrin (CD-streptavidin) which is assembled prior to assembly of the DOPC/DOPC biotinylated bilayer. Application of 0.5 V vs Ag/AgCl results in oxidation of the ferrocene, which in the presence of Na+ acquires a permanent positive charge, preventing reassembly of the CD-streptavidin. The released CD-streptavidin diffuses to the bilayer where its streptavidin pendant recognises and binds to biotin.

Such electrorelease can be combined with EIS to allow for the detection of interaction of released agent with the bilayer, and/or it can also be combined with spectroscopic methods, such as Raman and fluorescence spectroscopy for further investigation. It can be used for the controlled/timed release of a range of reagents asymmetrically bound to the bilayer, or, for example, of protein agonists to proteins within the bilayer and provides a method for addressing intercellular and extracellular binding sites on the same system.

In addition, to electrorelease for binding to a lipid or protein in the membrane, e.g. for signaling analogy, if an appropriate agent is employed it can be used to instigate the timed removal of reagent from the bilayer. The present inventors have demonstrated that the electrorelease of unlabeled CD to a cholesterol containing bilayer results in removal of cholesterol from the bilayer, reflected in a decrease in resistance of the bilayer film. In principle, the quantity of cholesterol removed can be controlled by altering the quantity of CD at the cavity through use of a mixed monolayer It will be appreciated that the above experimental data shows examples of applications of a microfluidic nanopore provided in accordance with the present teaching. By providing a plurality of depressions having a diameter greater than 1 µm and containing a solution it is possible to provide a lipid layer extending across the top of the depression which can then be used to mimic a cellular boundary. Such an array has application in a number of drug and other pharmaceutical investigatory studies and it is not intended to limit the present teaching to any one specific example except as may be deemed necessary in the light of the appended claims.

The words comprises/comprising when used in this specification are to specify the presence of stated features, integers, steps or components but does not preclude the presence or addition of one or more other features, integers, steps, components or groups thereof.

The invention claimed is:

1. A method for forming a microfluidic array comprising:
   forming a plurality of individual depressions in a planar surface of a hydrophilic polymeric substrate such that each of the plurality of individual depressions comprises arcuate side walls extending downwardly into the substrate from the planar surface and have a diameter greater than 1 µm and,
   filling the depressions with an aqueous solution; and
   forming a lipid layer extending across the plurality of individual depressions; wherein the method further comprises rendering the substrate hydrophilic by plasma treatment at a controlled air pressure.

2. The method of claim 1 wherein the lipid layer is a first lipid layer and the method further comprising forming a second lipid layer on the first lipid layer.

3. The method of claim 1 further comprising using Langmuir-Blodgett (LB) technique or LB Schaefer (LB S) technique for lipid layer formation.

4. The method of claim 2 wherein the second lipid layer is formed by fusion of liposomes over the first lipid layer.

5. The method of claim 1 wherein the substrate is formed of polydimethylsiloxane (PDMS).

6. The method of claim 3 wherein forming the plurality of individual depressions in the planar surface of a substrate comprises:
   coating an array of spheres with PDMS;
   allowing the PDMS to cure; and
   peeling the PDMS from the spheres to reveal a PDMS substrate.

7. The method of claim 1 wherein the depressions are filled with the aqueous solution using sonication.

8. The method of claim 1 further comprising:
   mounting the microfluidic array on a planar support; and
   forming an inlet and outlet at opposite ends of the substrate such that the inlet is configured for introduction of lipid vesicles to the array.

9. The method of claim 1 wherein the aqueous solution comprises proteo-liposomes.

10. The method of claim 1 further comprising, subsequent to formation lipid layer, using detergent treatment to introduce proteins to the lipid layer.

* * * * *